US012796946B2

(12) United States Patent
Endoh

(10) Patent No.: US 12,796,946 B2
(45) Date of Patent: Nov. 17, 2026

(54) MEASUREMENT DEVICE, OPTICAL SENSOR, BIOLOGICAL DATA MEASUREMENT SYSTEM, BIOLOGICAL INFORMATION ESTIMATION SYSTEM, MEASUREMENT METHOD, AND STORAGE MEDIUM

(71) Applicant: NEC Corporation, Tokyo (JP)

(72) Inventor: Hiroyuki Endoh, Tokyo (JP)

(73) Assignee: NEC CORPORATION, Tokyo (JP)

( * ) Notice: Subject to any disclaimer, the term of this patent is extended or adjusted under 35 U.S.C. 154(b) by 324 days.

(21) Appl. No.: 18/691,638

(22) PCT Filed: Dec. 10, 2021

(86) PCT No.: PCT/JP2021/045471
§ 371 (c)(1),
(2) Date: Mar. 13, 2024

(87) PCT Pub. No.: WO2023/105741
PCT Pub. Date: Jun. 15, 2023

(65) Prior Publication Data
US 2024/0374155 A1 Nov. 14, 2024

(51) Int. Cl.
*A61B 5/024* (2006.01)
*A61B 5/00* (2006.01)
(Continued)

(52) U.S. Cl.
CPC .......... *A61B 5/02427* (2013.01); *A61B 5/165* (2013.01); *A61B 5/742* (2013.01);
(Continued)

(58) Field of Classification Search
CPC .............. A61B 5/1455; A61B 5/14551; A61B 5/14552; A61B 5/1495; A61B 5/7221
See application file for complete search history.

(56) References Cited

U.S. PATENT DOCUMENTS

2013/0261415 A1* 10/2013 Ashe .................. A61B 5/14552
600/323
2017/0000350 A1* 1/2017 Kwon ................ A61B 5/14552
(Continued)

FOREIGN PATENT DOCUMENTS

JP H07-299043 A 11/1995
JP H11-164826 A 6/1999
(Continued)

OTHER PUBLICATIONS

International Search Report for PCT Application No. PCT/JP2021/045471, mailed on Mar. 1, 2022.
(Continued)

*Primary Examiner* — Eric F Winakur
(74) *Attorney, Agent, or Firm* — Sughrue Mion, PLLC

(57) ABSTRACT

Provided is a measurement device that outputs, to an optical sensor including a light receiving element array in which light receiving elements are two-dimensionally arranged, a measurement instruction including a first measurement instruction to instruct first measurement corresponding to preliminary measurement and a second measurement instruction to instruct second measurement corresponding to main measurement, acquires a reception signal of the light receiving elements according to the measurement instruction, generates biological data for the light receiving elements using the acquired reception signal, calculates a deviation of the biological data for the light receiving elements using the biological data generated using the reception signal acquired according to the first measurement instruction, and sets a measurement region including a light receiving element used for second measurement according to the second measurement instruction in accordance with the deviation of the biological data for the light receiving elements.

18 Claims, 26 Drawing Sheets

(51) Int. Cl.
*A61B 5/16* (2006.01)
*G16H 40/67* (2018.01)

(52) U.S. Cl.
CPC ...... *G16H 40/67* (2018.01); *A61B 2562/0238* (2013.01); *A61B 2562/0242* (2013.01); *A61B 2562/046* (2013.01)

(56) References Cited

U.S. PATENT DOCUMENTS

| | | | |
|---|---|---|---|
| 2017/0360316 A1 | 12/2017 | Gu et al. | |
| 2021/0103426 A1* | 4/2021 | Heo | G06F 1/163 |

FOREIGN PATENT DOCUMENTS

| | | |
|---|---|---|
| JP | 2005-198828 A | 7/2005 |
| JP | 2013-121420 A | 6/2013 |

OTHER PUBLICATIONS

English translation of Written opinion for PCT Application No. PCT/JP2021/045471, mailed on Mar. 1, 2022.

T. Yokota, et al., "A conformable imager for biometric authentication and vital sign measurement", Nature Electronics, vol. 3, pp. 113-121(2020).

JP Office Communication for JP Application No. 2023-565830, mailed on Mar. 18, 2025 with English Translation.

* cited by examiner

MEASUREMENT DEVICE, OPTICAL SENSOR, BIOLOGICAL DATA MEASUREMENT SYSTEM, BIOLOGICAL INFORMATION ESTIMATION SYSTEM, MEASUREMENT METHOD, AND STORAGE MEDIUM

This application is a National Stage Entry of PCT/JP2021/045471 filed on Dec. 10, 2021, the contents of all of which are incorporated herein by reference, in their entirety.

TECHNICAL FIELD

The present disclosure relates to a measurement device or the like that measures biological data using an optical sensor.

BACKGROUND ART

A measuring device that measures biological data such as a pulsatile waveform (pulse waveform) of an artery using an optical sensor has been developed. The activity of the autonomic nerve is reflected in the biological data such as the pulse. Therefore, a technique for estimating a subject's emotion using biological data has been developed. When emotion estimation is performed, it is preferable to constantly measure biological data.

NPL 1 discloses a flexible imaging device in which a high-resolution array-shaped sensor is mounted on a flexible substrate. The device of NPL 1 has a structure in which a polysilicon thin-film transistor readout circuit and an organic photodiode having high sensitivity in a near-infrared region are combined. The device of NPL 1 can acquire biological information such as a pulse or a vein image of a subject with high resolution by being attached to the skin of the subject.

PTL 1 discloses a measuring device that measures a pulse waveform. The device of PTL 1 includes a light source, a detection unit, and an analysis unit. The light source emits at least one kind of measurement light belonging to a predetermined wavelength band to a measurement region including at least part of a living body. In the detection unit, a plurality of sensors is regularly disposed in a predetermined arrangement. The detection unit detects the measurement light emitted from the light source and transmitted through the living body by the plurality of sensors. Using the detection result detected by the detection unit, the analysis unit performs analysis processing of identifying a measurement position for measuring information about pulsation associated with activity of a living body from the measurement region based on a change over time in the amount of light of the detected measurement light.

PTL 2 discloses a pulse detection device that detects a pulse. The device of PTL 2 includes a pulse detector including a plurality of sensors that includes a light emitting element and a light receiving element, the sensors receiving, by the light receiving element, reflected light or transmitted light of projection light from the light emitting element by a subject, and detecting a pulse by a change in an amount of light of the light receiving element. The device of PTL 2 detects the amplitude of the change in the amount of received light at the time of the pulse received by the light receiving element of each sensor included in the pulse detector. The device of PTL 2 compares magnitudes of amplitudes of changes in the amount of received light by a plurality of sensors, and identifies a sensor having the largest amplitude. The device of PTL 2 obtains the pulse rate by calculating the output signal of the sensor having the largest amplitude.

CITATION LIST

Patent Literature

PTL 1: JP 2013-121420 A

PTL 2: JP 7-299043 A

Non Patent Literature

NPL 1: T. Yokota, et al., "A conformable imager for biometric authentication and vital sign measurement", Nature Electronics, volume 3, p.p. 113-121 (2020).

SUMMARY OF INVENTION

Technical Problem

When the two-dimensional optical sensor is used as in Non-Patent Literature 1, a wide range of biological data can be measured at one measurement timing. As the number of elements of the light receiving element array constituting the two-dimensional optical sensor is larger, the pulse waveform can be reliably measured, but it is difficult to implement constant measurement due to power consumption, a communication speed, and the like. On the other hand, when the number of elements of the light receiving element array is small, measurement may be impossible due to a deviation of a measurement point due to body motion, and it is difficult to implement constant measurement.

According to the method of PTL 1, the pulse waveform can be accurately measured by identifying the measurement position from the measurement region based on the change over time of the amount of light of the measurement light. PTL 1 discloses calculating pulse waveform data in a minute region of interest by focusing on a change over time of data in the minute region. PTL 1 discloses calculating similarity between a pulse waveform measured in advance and pulse waveform data in each minute region using a pulse waveform measured in advance. Since there are factors such as drift and noise, it is not easy to calculate the similarity of the time series data of the pulse waveform data actually measured. Therefore, in the method of PTL 1, the measurement position cannot be appropriately identified from the measurement region, and it is difficult to constantly measure the biological data.

In the method of PTL 2, a sensor having the largest amplitude of the change in the amount of received light is selected, and the pulse rate is obtained using the output signal of the selected sensor. Therefore, the method of PTL 2 is less susceptible to factors such as drift and noise. In the method of PTL 2, in a case where the number of light receiving elements is about several, a sensor having the maximum amplitude of the change in the amount of received light can be identified. However, in the method of PTL 2, when the number of light receiving elements is about 10,000 pixels, it is difficult to identify a sensor having the maximum amplitude of the change in the amount of received light, and thus it is difficult to constantly measure the biological data.

An object of the present disclosure is to provide a measurement device or the like capable of implementing constant measurement of biological data using an optical sensor.

Solution to Problem

A measurement device according to an aspect of the present disclosure includes a measurement instruction output unit that outputs, to an optical sensor including a light receiving element array in which a plurality of light receiving elements is two-dimensionally arranged, a measurement instruction including a first measurement instruction to instruct first measurement corresponding to preliminary measurement and a second measurement instruction to instruct second measurement corresponding to main measurement, a reception signal acquisition unit that acquires a reception signal of at least one of the plurality of light receiving elements according to the measurement instruction, a biological data generation unit that generates biological data for each of the light receiving elements using the acquired reception signal, a calculation unit that calculates a deviation of the biological data for each of the light receiving elements using the biological data generated using the reception signal acquired according to the first measurement instruction, and a measurement region setting unit that sets a measurement region including a light receiving element used for second measurement according to the second measurement instruction in accordance with the deviation of the biological data for each of the light receiving elements.

In a measurement method according to an aspect of the present disclosure, the method includes outputting, to an optical sensor including a light receiving element array in which a plurality of light receiving elements is two-dimensionally arranged, a measurement instruction including a first measurement instruction to instruct first measurement corresponding to preliminary measurement and a second measurement instruction to instruct second measurement corresponding to main measurement, acquiring a reception signal of at least one of the plurality of light receiving elements according to the measurement instruction, generating biological data for each of the light receiving elements using the acquired reception signal, calculating a deviation of the biological data for each of the light receiving elements using the biological data generated using the reception signal acquired according to the first measurement instruction, and setting a measurement region including a light receiving element used for second measurement according to the second measurement instruction in accordance with the deviation of the biological data for each of the light receiving elements.

In a program according to an aspect of the present disclosure, the program causes a computer to execute the steps of outputting, to an optical sensor including a light receiving element array in which a plurality of light receiving elements is two-dimensionally arranged, a measurement instruction including a first measurement instruction to instruct first measurement corresponding to preliminary measurement and a second measurement instruction to instruct second measurement corresponding to main measurement, acquiring a reception signal of at least one of the plurality of light receiving elements according to the measurement instruction, generating biological data for each of the light receiving elements using the acquired reception signal, calculating a deviation of the biological data for each of the light receiving elements using the biological data generated using the reception signal acquired according to the first measurement instruction, and setting a measurement region including a light receiving element used for second measurement according to the second measurement instruction in accordance with the deviation of the biological data for each of the light receiving elements.

Advantageous Effects of Invention

According to the present disclosure, it is possible to provide a measurement device or the like capable of implementing constant measurement of biological data using an optical sensor.

EXAMPLE EMBODIMENT

Figure 1:
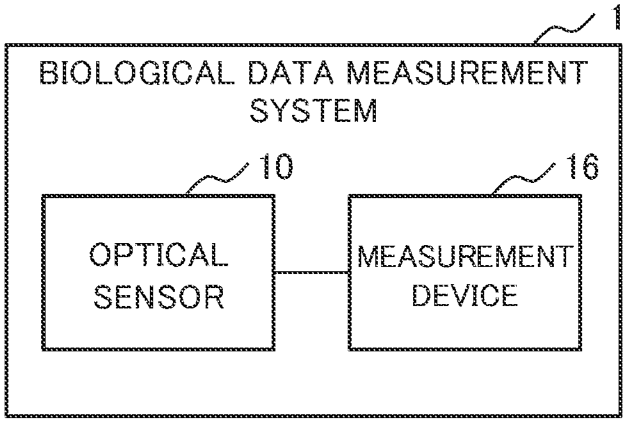
FIG. 1 is a block diagram illustrating an example of a configuration of a biological data measurement system according to a first example embodiment.

Hereinafter, embodiments of the present invention will be described with reference to the drawings. However, the example embodiments described below have technically preferable limitations for carrying out the present invention, but the scope of the present invention is not limited to the following. In all the drawings used in the following description of the example embodiment, the same reference numerals are given to the same parts unless there is a particular reason. In the following example embodiments, repeated description of similar configurations and operations may be omitted.

First Example Embodiment

First, a biological data measurement system according to a first example embodiment will be described with reference to the drawings. The biological data measurement system according to the present example embodiment measures the pulsation (pulse) of the artery according to the received light signal detected by the optical sensor attached to the skin of the subject. Hereinafter, an example of measuring a pulse as biological data will be described. The method of the present example embodiment can also be applied to measurement of biological data other than pulse as long as the measurement is performed using an optical sensor.

(Configuration)

FIG. 1 is a block diagram illustrating an example of a configuration of a biological data measurement system 1 according to the present example embodiment. The biological data measurement system 1 includes an optical sensor 10 and a measurement device 16. The optical sensor 10 is attached to the human body of the subject. The measurement device 16 is mounted on a portable terminal (not illustrated) carried by the subject. The measurement device 16 may be constructed in a cloud or a server connectable via a portable terminal carried by the subject.

The optical sensor 10 includes a light receiving element array in which a plurality of light receiving elements is arranged in an array. The optical sensor 10 emits light from above the skin of the subject and receives reflected light of the light. The measurement device 16 measures the pulsation (pulse) of the artery according to the received light signal measured by the optical sensor 10 attached to the skin of the subject. The measurement device 16 measures the pulse of the subject according to the intensity change of the received reflected light. Hereinafter, the optical sensor 10 and the measurement device 16 will be individually described.

[Optical Sensor]

Figure 2:
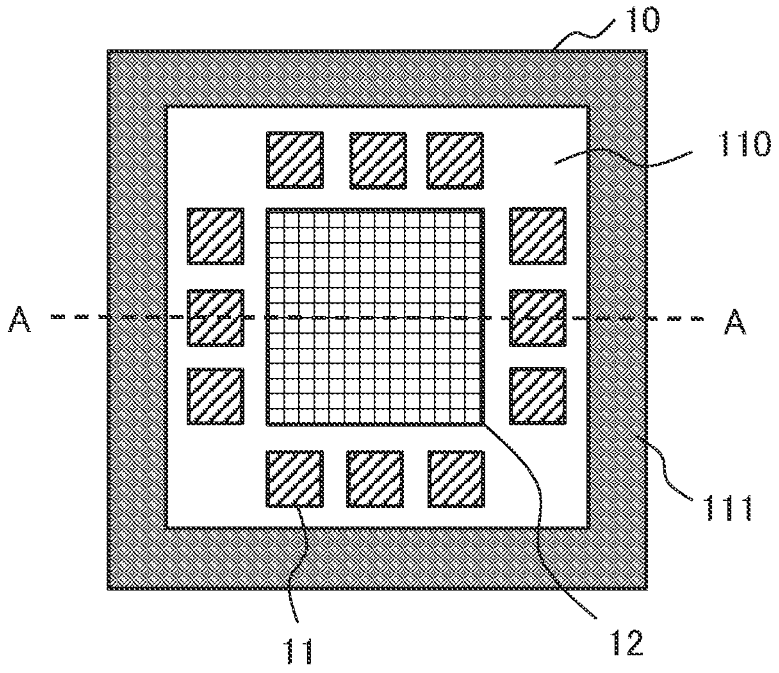
FIG. 2 is a conceptual diagram illustrating an example of a measurement face of an optical sensor included in the biological data measurement system according to the first example embodiment.
Figure 3:
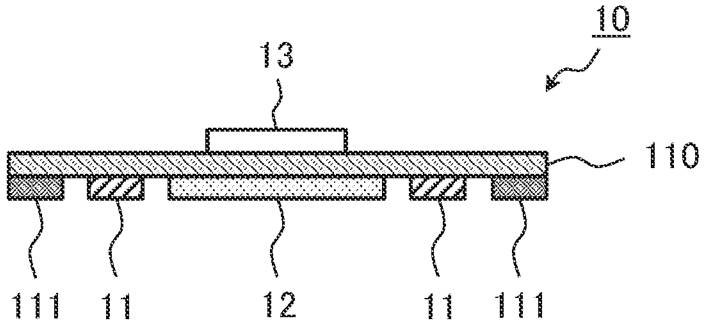
FIG. 3 is a cross-sectional view illustrating an example of a configuration of an optical sensor included in the biological data measurement system according to the first example embodiment.

FIGS. 2 to 3 are conceptual diagrams illustrating an example of a configuration of the optical sensor 10. FIG. 2 is a view of the optical sensor 10 when viewing a measurement face. FIG. 3 is a cross-sectional view of the optical sensor 10 taken along line A-A in FIG. 2. The optical sensor 10 includes a plurality of light emitters 11, a light receiving element array 12, and a control unit 13.

The plurality of light emitters 11, the light receiving element array 12, and the control unit 13 are disposed on the surface of a substrate 110. The plurality of light emitters 11 and the light receiving element array 12 are formed on a first face (also referred to as a measurement face) of the substrate 110. An adhesive layer 111 for attaching the optical sensor 10 to the skin of the subject is installed around the plurality of light emitters 11 and the light receiving element array 12. The optical sensor 10 is attached to the skin of the subject in such a way that light from the outside does not enter a space at the measurement face of the substrate 110 in a state of being attached to the skin. FIG. 3 illustrates an example in which the control unit 13 is disposed on a face opposite to the measurement face. The position where the control unit 13 is disposed is not limited to the face opposite to the measurement face. For example, the control unit 13 may be disposed inside the substrate 110 or at a position away from the plurality of light emitters 11 and the light receiving element array 12.

The light emitter 11 has an emission face that emits light used for measuring pulse. The light emitted from the light emitter 11 at the time of pulse measurement is also referred to as an optical signal. The plurality of light emitters 11 is disposed with their emission faces having the same direction. The emission faces of the plurality of light emitters 11 and the light receiving face of the light receiving element array 12 are disposed with the same direction. The emission face of the light emitter 11 faces the skin of the subject in a state where the optical sensor 10 is attached to the skin of the subject.

FIG. 2 illustrates an example in which 12 light emitters 11 are disposed along four sides of the light receiving element array 12. The number of the light emitters 11 is not limited to 12. The positions where the light emitters 11 are disposed may not be disposed along the four sides of the light receiving element array 12. As long as the optical signal emitted from the light emitter 11 can be received by the light receiving element array 12, the position where the light emitter 11 is disposed is not limited.

The light emitter 11 emits an optical signal of a wavelength band in which a pulse can be measured according to the control of the control unit 13. For example, the light emitter 11 is achieved by a light-emitting diode (LED). For example, the light emitter 11 emits an optical signal in a green wavelength band. For pulse measurement, an optical signal in a green wavelength band is preferable. For example, the light emitter 11 emits an optical signal in a near-infrared wavelength band. In the case of measuring the entire vein, for example, near infrared rays of about 1.1 micrometers are suitable. For example, when the plurality of light emitters 11 can emit the red wavelength band and the infrared wavelength band, the arterial oxygen saturation can be measured according to the difference in absorbance therebetween. The wavelength band of the optical signal emitted from the light emitter 11 is not particularly limited as long as it is a wavelength band in which biological data can be measured. The optical outputs of the plurality of light emitters 11 may be the same or different. The optical output of the plurality of light emitters 11 may be constant or adjustable. When the optical outputs of the plurality of light emitters 11 are adjustable, the optical output can be adjusted for each light emitter 11.

The light receiving element array 12 has a light receiving face that receives reflected light of the optical signal emitted from the light emitter 11. The reflected light is a light component that is reflected/scattered under the skin (inside the body) of the subject and reaches the light receiving face of the light receiving element array 12 in the optical signal emitted from the light emitter 11. On the light receiving face of the light receiving element array 12, a plurality of light receiving elements is disposed in a two-dimensional array. For example, about 10,000 light receiving elements are disposed in a two-dimensional array on the light receiving face of the light receiving element array 12. The light intensity of the reflected light received by each of the plurality of light receiving elements disposed in a two-dimensional array is measured in association with the positions (addresses) of the light receiving elements.

For example, the light receiving element array 12 can be achieved by a sheet type image sensor disclosed in NPL 1 (NPL 1: T. Yokota, et al., "A conformable imager for biometric authentication and vital sign measurement", Nature Electronics, volume 3, p.p. 113-121 (2020)). The sheet type image sensor of NPL 1 has a configuration in which an organic photodiode, a thin-film transistor, a complementary metal-oxide semiconductor (CMOS), and a light detector are combined. In the present example embodiment, the light emitter 11 and the light receiving element array 12 are configured separately, but the light emitter 11 and the light receiving element array 12 may be integrated as in the sheet-type image sensor of NPL 1.

Figure 4:
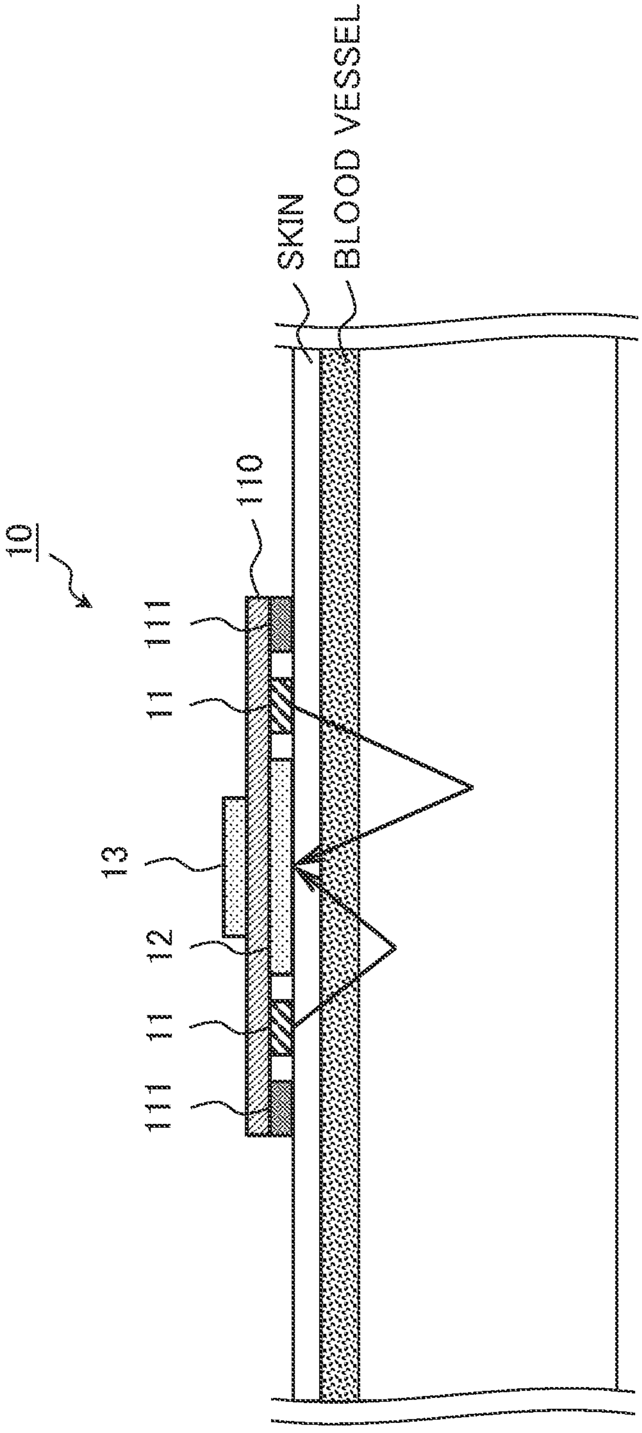
FIG. 4 is a conceptual diagram for describing a position example of emission and reception of an optical signal by an optical sensor included in the biological data measurement system according to the first example embodiment.

FIG. 4 is a conceptual diagram illustrating a state in which the optical signal emitted from the light emitter 11 is reflected/scattered under the skin (in the body) of the subject. The reflected light of the optical signal emitted from each of the plurality of light emitters 11 is received by the light receiving element array 12 via different paths. The light intensity of the optical signals emitted from the plurality of light emitters 11 changes according to light absorption characteristics and scattering characteristics by body constituent tissues such as skin, blood vessels, muscles, fat, and bone. Therefore, the light intensity of the reflected light received by the light receiving element varies according to the length of the path of the optical signal/reflected light, the environment under the skin, and the body motion of the subject. In the present example embodiment, an optical signal is emitted from the light emitter 11 from above the skin of the subject toward the body, and the pulse of the subject is measured according to reflected light of the optical signal. For example, in the present example embodiment, a variation in the blood volume in the body due to pulsation is measured as a change in absorbance (also referred to as a light intensity change).

Figure 5:
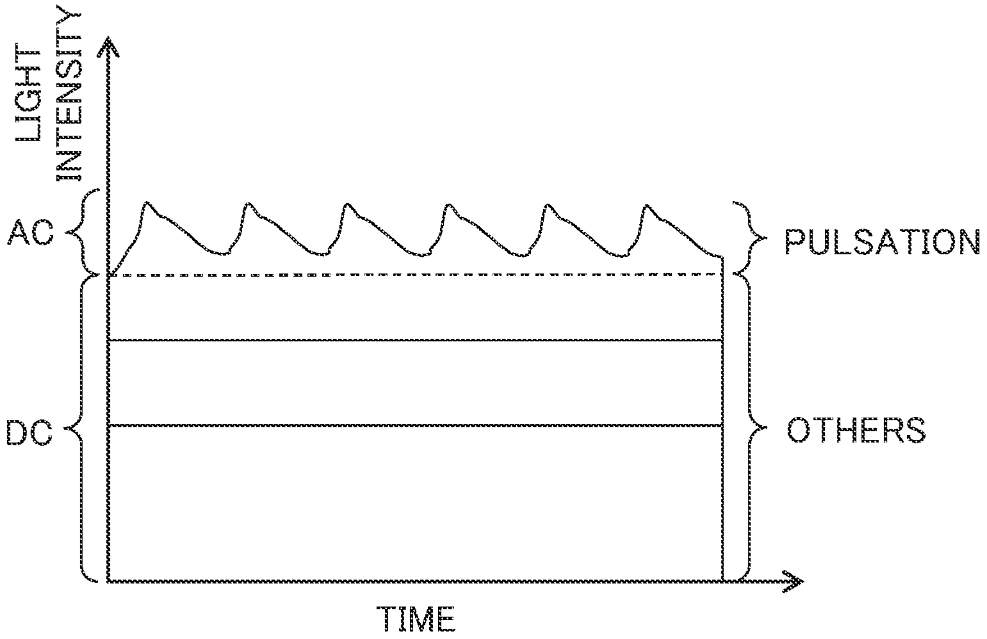
FIG. 5 is a graph for describing an example of reflected light received by a light receiving element array of an optical sensor included in the biological data measurement system according to the first example embodiment.

FIG. 5 is a graph for describing an example of reflected light received by the light receiving element array 12. The reflected light includes a fluctuation component and a stationary component. The fluctuation component is also referred to as an alternating current (AC) component. The AC component fluctuates due to pulsation. The stationary component is also referred to as a direct current (DC) component. The DC component hardly fluctuates due to pulsation. The pulse is measured based on the light intensity change of the reflected light according to the fluctuation of the AC component. In the present example embodiment, the fluctuation of the AC component is measured as pulsation.

The control unit 13 controls the plurality of light emitters 11. For example, the control unit 13 is achieved by a microcomputer or a microcontroller. For example, the control unit 13 includes a central processing unit (CPU), a random access memory (RAM), a read only memory (ROM), a flash memory, and the like. The control unit 13 executes control and processing according to a program stored in advance. The control unit 13 executes control and processing according to the program in accordance with a preset schedule, an instruction from the outside, or the like.

Figure 6:
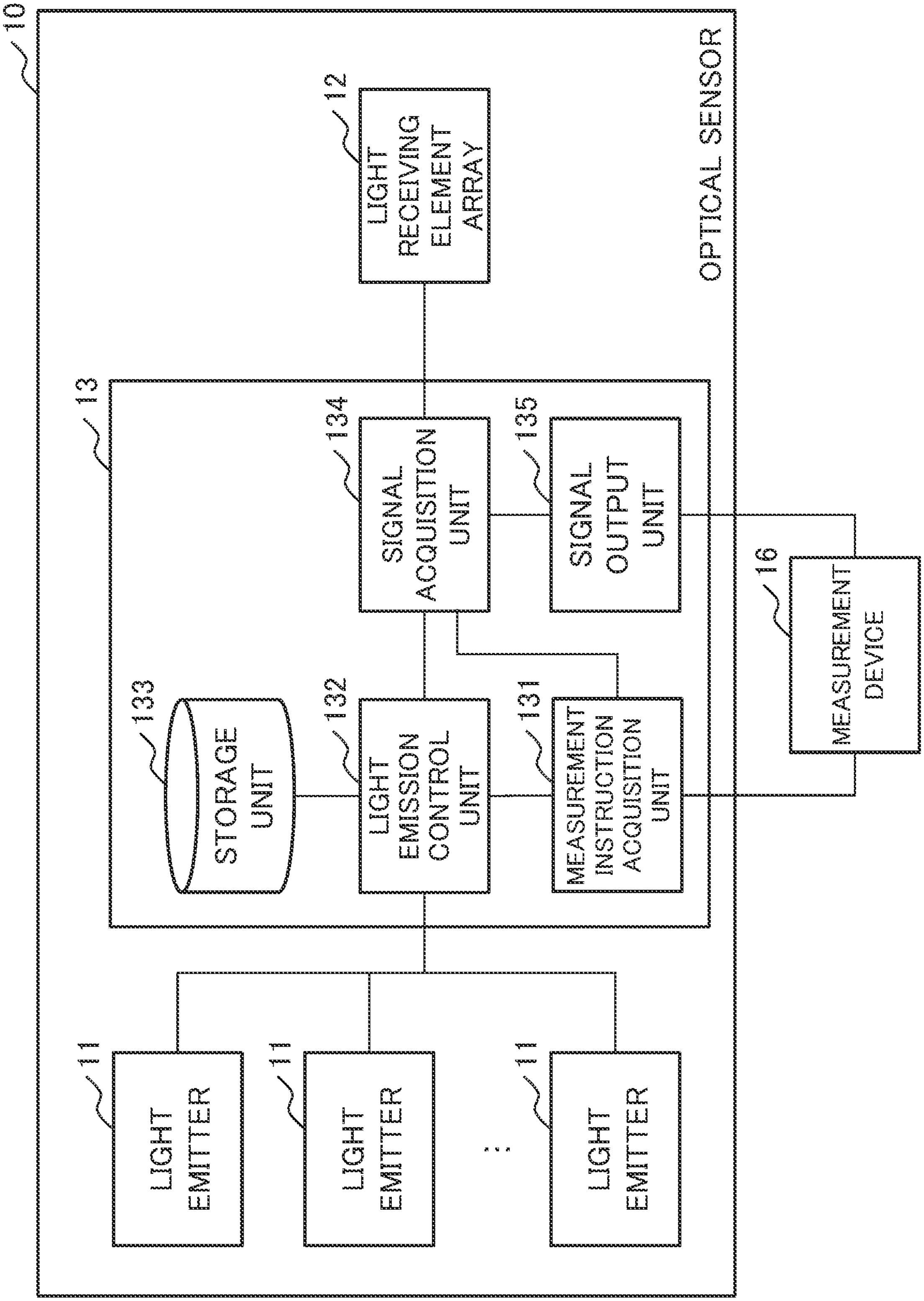
FIG. 6 is a block diagram illustrating an example of a configuration of an optical sensor included in the biological data measurement system according to the first example embodiment.

FIG. 6 is a block diagram illustrating an example of a function configuration of the optical sensor 10. The control unit 13 includes a measurement instruction acquisition unit 131, a light emission control unit 132, a storage unit 133, a signal acquisition unit 134, and a signal output unit 135.

The measurement instruction acquisition unit 131 acquires the measurement instruction from the measurement device 16. The measurement instruction acquisition unit 131 acquires an instruction to perform preliminary measurement (also referred to as a first measurement instruction) from the measurement device 16. The first measurement instruction is an instruction to perform preliminary measurement for a certain period in all the light receiving elements of the light receiving element array 12. The measurement instruction acquisition unit 131 outputs the acquired first measurement instruction to the light emission control unit 132 and the signal acquisition unit 134. The measurement instruction acquisition unit 131 acquires an instruction (also referred to as a second measurement instruction) to perform measurement in a measurement channel to be described later from the measurement device 16. The second measurement instruction is an instruction to perform continuous main measurement in a selected measurement channel among the light receiving elements of the light receiving element array 12. The selected measurement channel forms a measurement region. The measurement instruction acquisition unit 131 outputs the acquired second measurement instruction to the light emission control unit 132 and the signal acquisition unit 134.

The light emission control unit 132 acquires a measurement instruction by the measurement device 16 from the measurement instruction acquisition unit 131. The light emission control unit 132 acquires a first measurement instruction to perform preliminary measurement from the measurement instruction acquisition unit 131. The light emission control unit 132 performs control to cause the plurality of light emitters 11 to emit light in response to the first measurement instruction. The light emission control unit 132 controls the plurality of light emitters 11 by a control method according to the first measurement instruction stored in the storage unit 133. The light emission control unit 132 acquires a second measurement instruction to perform continuous measurement (main measurement) from the measurement instruction acquisition unit 131. The light emission control unit 132 performs control to cause the plurality of light emitters 11 to emit light in response to the second measurement instruction. The light emission control unit 132 controls the plurality of light emitters 11 by a control method according to the second measurement instruction stored in the storage unit 133. For example, the light emission control unit 132 similarly controls all of the plurality of light emitters 11 according to the first measurement instruction and the second measurement instruction. For example, the light emission control unit 132 may control each of the plurality of light emitters 11 in a different pattern according to the first measurement instruction and the second measurement instruction. A method of controlling the plurality of light emitters 11 by the light emission control unit 132 is not particularly limited.

The storage unit 133 stores a control method for causing the plurality of light emitters 11 to emit light. The control method stored in the storage unit 133 is referred to by the light emission control unit 132. The control method stored in the storage unit 133 is not particularly limited.

The signal acquisition unit 134 acquires a measurement instruction by the measurement device 16 from the measurement instruction acquisition unit 131. The signal acquisition unit 134 acquires the first measurement instruction to perform the preliminary measurement from the measurement instruction acquisition unit 131. In response to the first measurement instruction, the signal acquisition unit 134 acquires a received light signal related to the reflected light received by each of all the light receiving elements constituting the light receiving element array 12. The signal acquisition unit 134 outputs the received light signals of all the light receiving elements to the signal output unit 135. The signal acquisition unit 134 acquires a second measurement instruction to perform continuous measurement (main measurement) from the measurement instruction acquisition unit 131. In response to the second measurement instruction, the signal acquisition unit 134 acquires a received light signal related to the reflected light received by the light receiving element set to the measurement channel selected by the measurement device 16. The signal acquisition unit 134 outputs the received light signal of the light receiving element set in the measurement channel to the signal output unit 135.

The signal output unit 135 acquires the reception signal from the signal acquisition unit 134. The signal output unit 135 outputs the acquired reception signal to the measurement device 16. For example, the signal output unit 135 may store the reception signals acquired from the light receiving element array 12 in a storage device such as a flash memory, and collectively transmit the reception signals in a predetermined period to the measurement device 16.

The substrate 110 is a bendable substrate. The substrate 110 has a bendable plate-like shape. For example, the substrate 110 has a structure in which a conductive layer such as a copper foil is formed on a face of a polyimide base layer, and the conductive layer is laminated with a covering layer of a plastic film. For example, the base layer and the covering layer of the substrate 110 may be mainly composed of a urethane nonwoven fabric, vinyl chloride, a stretchable cotton fabric, a sponge sheet, a urethane film, or an olefin film. The light emitter 11, the light receiving element array 12, and the control unit 13 mounted on the substrate 110 may be configured to be deformed or may be configured not to be deformed according to the deformation of the substrate 110.

A plurality of light emitters 11 and a light receiving element array 12 are disposed on a measurement face (also referred to as a first face) of the substrate 110. The adhesive layer 111 is formed in a peripheral portion of the measurement face of the substrate 110. The portion where the adhesive layer 111 is formed may have a material or structure different from those of the other portions. For example, when the portion where the adhesive layer 111 is formed has a mesh-like structure, the portion of the adhesive layer 111 is less likely to be stuffy, and a decrease in adhesive force of the adhesive layer 111 due to sweat or the like can be suppressed. The control unit 13 is disposed on the second face facing the measurement face of the substrate 110. The control unit 13 may be disposed inside the substrate 110. For example, in order to improve the waterproof property, the control unit 13 may be disposed inside the substrate 110. For example, in order to improve the waterproof property, the control unit 13 may be covered with a waterproof film or the like. For example, when the optical sensor 10 is attached to the body of the subject, the substrate 110 is deformed according to the shape of the portion to be attached. The material, structure, and shape of the substrate 110 are not particularly limited.

The adhesive layer 111 is formed at a peripheral portion of the measurement face of the substrate 110. The adhesive layer 111 includes an adhesive for attaching the optical sensor 10 to the body of the subject. For example, the adhesive layer 111 includes an acrylic adhesive, a rubber adhesive, or a silicone adhesive. The adhesive layer 111 preferably has a light shielding property in such a way that light from the outside does not reach the light emitter 11 and the light receiving element array 12. The material of the adhesive layer 111 is not particularly limited. For example, it is preferable to use a material that is less irritating to the skin for the adhesive layer 111. For example, the adhesive layer 111 may contain a substance that reduces discomfort to the skin. For example, the adhesive layer 111 may contain menthol or the like. For example, the adhesive layer 111 may contain a substance that suppresses a decrease in adhesive force due to absorption of moisture such as sweat. For example, the adhesive layer 111 may contain a polymer absorber or the like. In the present example embodiment, an example in which the optical sensor 10 is attached to the body of the subject by the adhesive layer 111 is shown, but the optical sensor 10 may be attached to the body of the subject by a band (not shown) or the like.

[Measurement Device]

Figure 7:
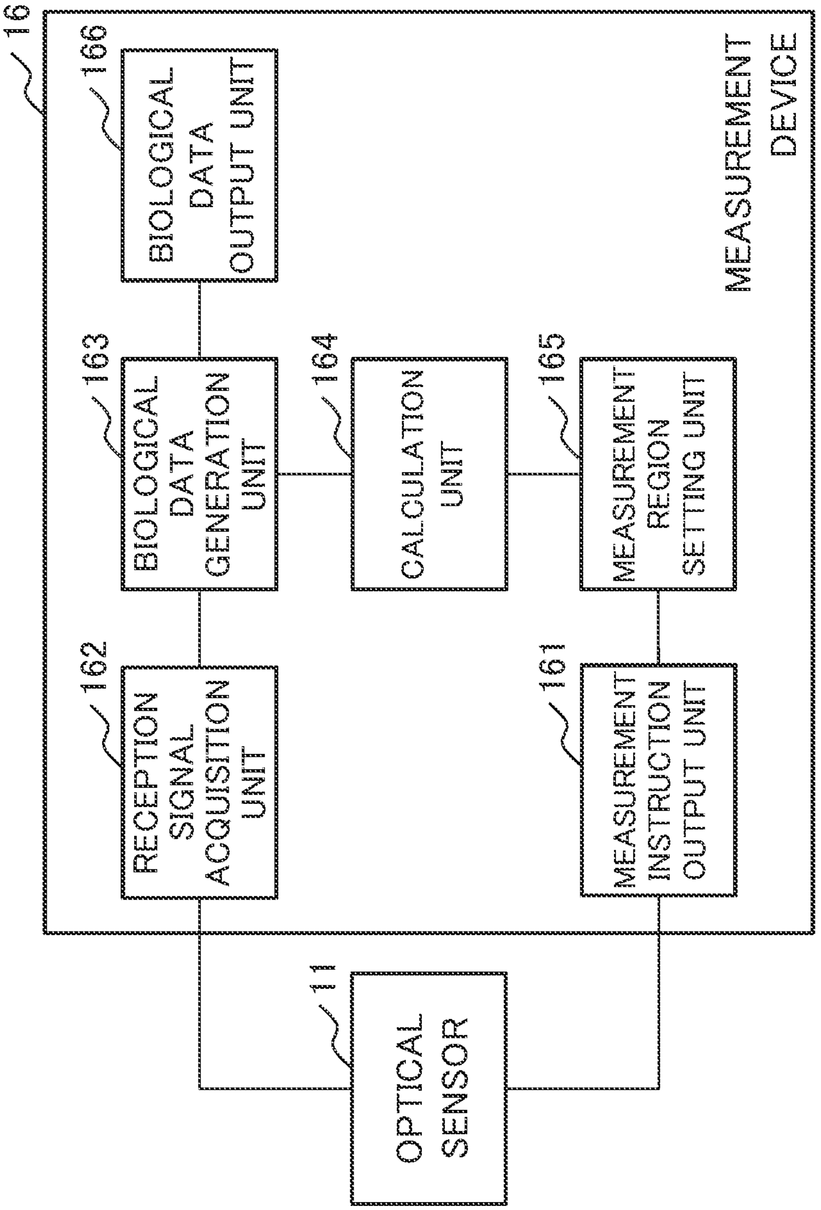
FIG. 7 is a block diagram illustrating an example of a configuration of a measurement device included in the biological data measurement system according to the first example embodiment.

FIG. 7 is a block diagram illustrating an example of a function configuration of the measurement device 16. The measurement device 16 includes a measurement instruction output unit 161, a reception signal acquisition unit 162, a biological data generation unit 163, a calculation unit 164, a measurement region setting unit 165, and a biological data output unit 166.

When the measurement device 16 is activated, the measurement instruction output unit 161 outputs a first measurement instruction to perform preliminary measurement to the optical sensor 10 prior to the continuous main measurement. The first measurement instruction is an instruction to perform preliminary measurement for a certain period in all the light receiving elements of the light receiving element array 12. The measurement instruction output unit 161 acquires the address of the measurement channel selected by the measurement region setting unit 165. The measurement instruction output unit 161 outputs a second measurement instruction to perform measurement in the selected measurement channel to the optical sensor 10. The second measurement instruction is an instruction to perform continuous main measurement in a selected measurement channel among the light receiving elements of the light receiving element array 12.

The measurement instruction output unit 161 outputs the first measurement instruction to the optical sensor 10 in order to update the measurement channel at a predetermined update timing. For example, the measurement instruction output unit 161 may output an instruction to perform the first measurement instruction to the optical sensor 10 with respect to the region including the measurement channel being measured. The measurement instruction output unit 161 may update the measurement channel according to the value or variation of the biological data during the main measurement.

The reception signal acquisition unit 162 acquires a reception signal according to the measurement instruction of the measurement instruction output unit 161 from the optical sensor 10. The reception signal according to the first measurement instruction is a signal from all the light receiving elements constituting the light receiving element array 12 of the optical sensor 10. The reception signal according to the second measurement instruction is a signal from the light receiving element set to the measurement channel among the plurality of light receiving elements constituting the light receiving element array 12 of the optical sensor 10. The reception signal acquisition unit 162 outputs the acquired reception signal to the biological data generation unit 163. For example, the reception signal acquisition unit 162 may store the reception signal acquired from the light receiving element array 12 in a flash memory (not illustrated).

The biological data generation unit 163 acquires a reception signal according to the measurement instruction of the measurement instruction output unit 161 from the reception signal acquisition unit 162. The biological data generation unit 163 generates biological data using the acquired reception signal. For example, the biological data generation unit 163 generates pulse data using time series data of the acquired reception signal. The biological data generated by the biological data generation unit 163 is not particularly limited.

The biological data generation unit 163 outputs the biological data generated using the reception signal according to the first measurement instruction to the calculation unit 164. On the other hand, the biological data generation unit 163 outputs the biological data generated using the reception signal according to the second measurement instruction to the biological data output unit 166. For example, at a predetermined verification timing, the biological data generation unit 163 may output the biological data generated using the reception signal according to the second measurement instruction to the calculation unit 164. The biological data output to the calculation unit 164 at the verification timing is used for verification of the measurement channel being selected. For example, the biological data generation unit 163 may store the generated biological signal in a flash memory (not illustrated).

Figure 8:
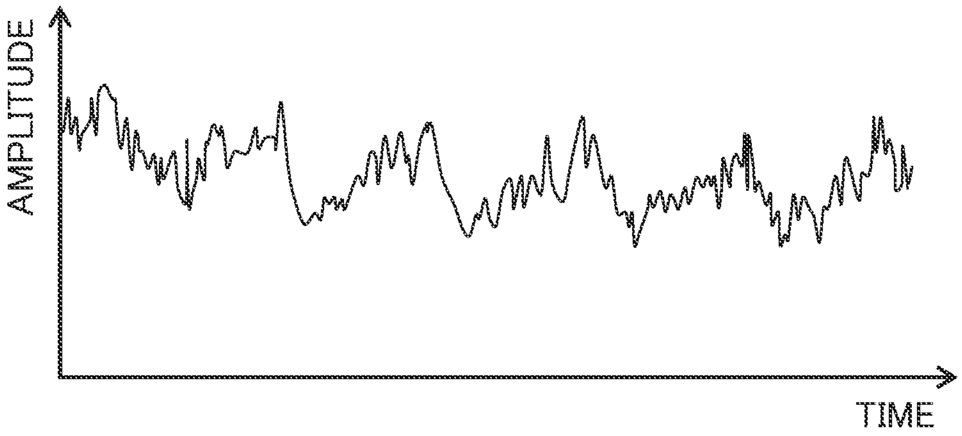
FIG. 8 is an example of time series data of biological data measured for each light receiving element constituting a light receiving element array of an optical sensor included in the biological data measurement system according to the first example embodiment.

FIG. 8 is an example of time series data of biological data (pulsation) generated based on a measurement value (amplitude) for each channel. The time series data of the biological data (pulsation) in FIG. 8 includes several pulsations. For example, the difference between the maximum value and the minimum value of each pulsation is the representative value of the channel. As illustrated in FIG. 8, the biological data based on the measurement value for each channel includes drift and noise. Therefore, it is difficult to compare the measurement values of the plurality of light receiving elements (channels) constituting the light receiving element array 12 with the average value for each channel. In the present example embodiment, the measurement values of the plurality of light receiving elements (channels) constituting the light receiving element array 12 are easily compared by using the deviation of the measurement values for each channel. When the biological data is measured without omission in the plane of the light receiving face of the light receiving element array 12, the measurement values of all the light receiving elements are required. For example, in a case where the number of the light receiving elements of the light receiving element array 12 are 120×160 pixels, it is difficult to use the measurement values of all the light receiving elements due to restrictions such as communication speed. For example, in a case where biological data is used for emotion estimation, it is difficult to collect biological data for 10,000 pixels in real time, which requires a resolution of about 100 Hz (hertz). In the present example embodiment, since the light receiving element to be used for measurement of the biological data is selected from the light receiving elements constituting the light receiving element array 12, the load of calculation and communication can be reduced.

The calculation unit 164 selects a channel on which the main measurement is performed using the biological data based on the reception signal received in response to the first measurement instruction. The calculation unit 164 calculates a representative value of the amplitude of the biological data for each channel for all of the plurality of light receiving elements (channels) constituting the light receiving element array 12. For example, the calculation unit 164 calculates the maximum value of the amplitude of the biological data as the representative value for each channel. The calculation unit 164 calculates an average value of representative values of the plurality of light receiving elements (channels) constituting the light receiving element array 12. The calculation unit 164 calculates, for each channel, a deviation (also referred to as a channel deviation) obtained by subtracting an average value of representative values of a plurality of light receiving elements (channels) from a representative value of each light receiving element (channel). The calculation unit 164 outputs the channel deviation calculated for each channel to the measurement region setting unit 165.

For example, assuming that the number of light receiving elements of the light receiving element array 12 is m, the calculation unit 164 can calculate the channel deviation $D_m$ of the channel m using the following Formula 1 (m is a natural number).

$$D_m = M_m - A \quad (1)$$

In the above Formula 1, $M_m$ is the maximum value of the biological data (amplitude) of the channel m. A is an average value of the maximum values of the biological data (amplitudes) related to the plurality of light receiving elements (channels).

Figure 9:
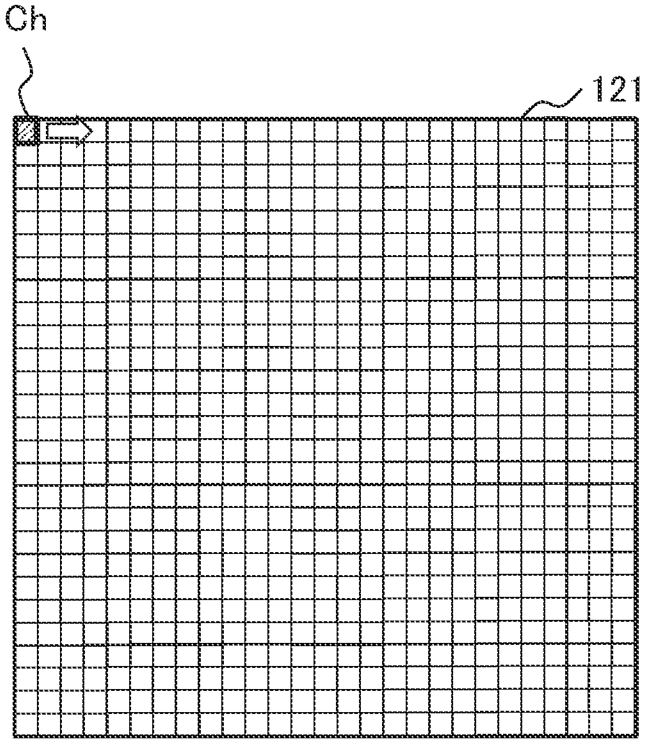
FIG. 9 is a conceptual diagram for describing a measurement channel setting process by the measurement device included in the biological data measurement system according to the first example embodiment.

FIG. 9 is a conceptual diagram for describing an example of calculating a channel deviation obtained by subtracting an average value from a representative value for each light receiving element (channel Ch) constituting the light receiving element array 12. FIG. 9 illustrates a pixel image 121 related to the light receiving face of the light receiving element array 12. The example of FIG. 9 illustrates a state in which the channel deviation is calculated with respect to the biological data based on the reception signal received by the upper left light receiving element (channel). The channel deviation may be collectively calculated for the plurality of light receiving elements (channels) constituting the light receiving element array 12. In the case of the example of FIG. 9, the calculation unit 164 calculates the channel deviation for all of the plurality of light receiving elements (channels). For example, the calculation unit 164 may calculate the channel deviation by narrowing the range instead of all the light receiving elements (channels) constituting the light receiving element array 12.

The calculation unit 164 may calculate the deviation of the measurement values of the plurality of light receiving elements (channels) constituting the light receiving element array 12 not for single channel but for plurality of channels. For example, the control unit 13 may set a region including 4 channels of 2× 2 (referred to as a calculation region) and calculate a deviation of a measurement value for each calculation region. For example, the control unit 13 calculates a value obtained by subtracting the average value of the representative values of the plurality of light receiving elements (channels) from the average value of the representative values of the measurement values by the light receiving elements (channels) included in the calculation region as a deviation (also referred to as a region deviation) of the calculation region. The calculation unit 164 outputs the region deviation calculated for each calculation region to the measurement region setting unit 165.

The arrangement of the calculation regions can be set in any arrangement as well as 2×2. For example, the number and arrangement of channels included in the calculation region are set in advance. The number and arrangement of channels included in the calculation region may be automatically set according to a selection situation of channels included in a measurement candidate region to be described later. For example, the calculation unit 164 changes the number and arrangement of channels included in the calculation region according to the number of channels included in the measurement candidate region.

Figure 10:
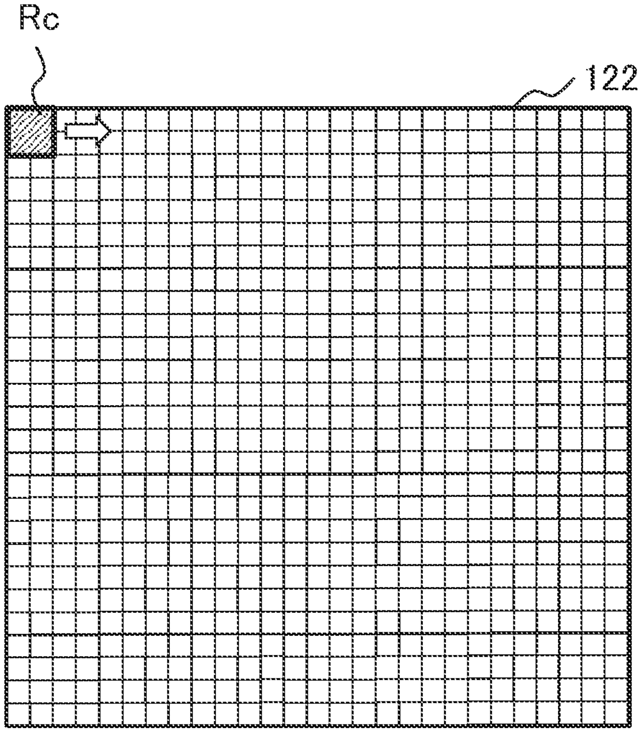
FIG. 10 is a conceptual diagram for describing a measurement channel setting process by the measurement device included in the biological data measurement system according to the first example embodiment.

FIG. 10 is a conceptual diagram for describing an example of calculating a region deviation obtained by subtracting an average value from a representative value for each calculation region $R_c$ including 4 light receiving elements of 2×2. FIG. 10 is a pixel image 122 related to the light receiving face of the light receiving element array 12. The example of FIG. 10 illustrates a state in which the region deviation is calculated with respect to the biological data based on the reception signals received by the plurality of light receiving elements (channels) included in the upper left calculation region $R_c$. The region deviation may be collectively calculated for the plurality of calculation regions $R_c$ set in the plurality of light receiving elements (channels) constituting the light receiving element array 12. In the case of the example of FIG. 10, the calculation unit 164 calculates the region deviation for all of the plurality of calculation regions $R_c$. For example, the calculation unit 164 may calculate the region deviation by narrowing the range instead of the plurality of calculation regions $R_c$ set for all of the plurality of light receiving elements (channels) constituting the light receiving element array 12. The calculation unit 164 may set the calculation region $R_c$ not only for the 4 light receiving elements of 2×2 but also for an any number of light receiving elements. For example, the plurality of light receiving elements (channels) may be shared by the plurality of calculation regions $R_c$.

The calculation unit 164 calculates a standard deviation of channel deviations calculated for a plurality of light receiving elements (channels). The calculation unit 164 outputs the calculated standard deviation of the channel deviations related to the plurality of light receiving elements (channels) to the measurement region setting unit 165.

The measurement region setting unit 165 acquires the channel deviation calculated for each channel, the region deviation calculated for each calculation region, and the standard deviation of the channel deviations regarding the plurality of light receiving elements (channels) from the calculation unit 164. The measurement region setting unit 165 selects a channel (also referred to as a measurement channel) to be used for main measurement of the biological data based on the channel deviation and the region deviation. For example, the measurement region setting unit 165 sets a region of a channel in which a deviation such as a channel deviation or a region deviation exceeds a predetermined threshold value as the measurement candidate region. For example, the measurement region setting unit 165 selects a measurement channel based on a comparison result between a deviation such as a channel deviation or a region deviation and a standard deviation of channel deviations related to a plurality of light receiving elements (channels). For example, the measurement region setting unit 165 sets, as the measurement candidate region, the light receiving element (channel) in which the deviation such as the channel deviation and the region deviation is equal to or more than 1.5 times the standard deviation of the channel deviations related to the plurality of light receiving elements (channels). The measurement region setting unit 165 selects a measurement channel from the light receiving elements (channels) set as the measurement candidate regions. The measurement region setting unit 165 sets the selected measurement channel for the measurement region.

Figure 11:
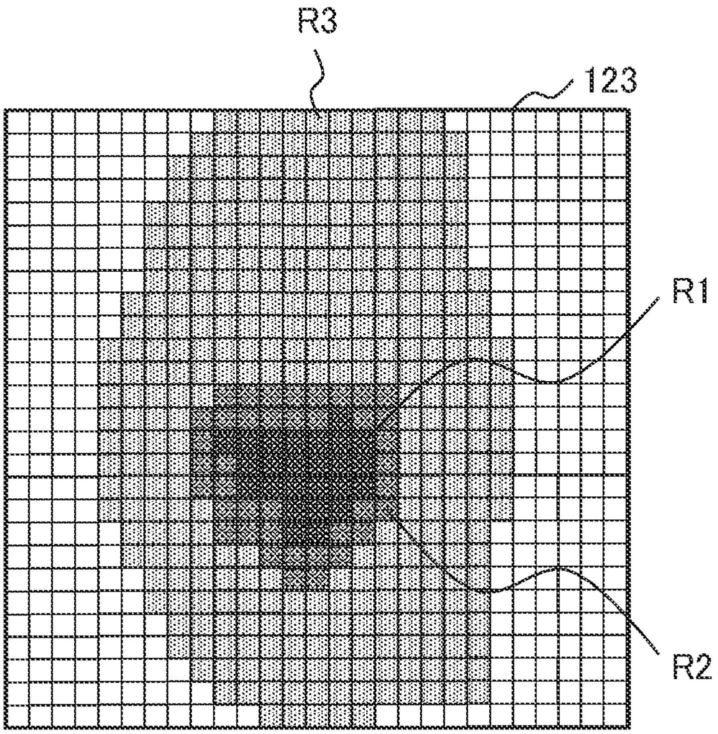
FIG. 11 is a heat map in which the position of the light receiving element in which the deviation calculated by the measurement device of the biological data measurement system according to the first example embodiment is larger than the standard deviation of the channel deviations regarding the plurality of light receiving elements is mapped in association with the light receiving face of the light receiving element array.

FIG. 11 is a heat map in which the position of the light receiving element (channel) in which the deviation calculated by the measurement device 16 is larger than the standard deviation of the channel deviations regarding the plurality of light receiving elements (channels) is mapped in association with the light receiving face of the light receiving element array 12. FIG. 11 is a pixel image 123 related to the light receiving face of the light receiving element array 12. In the example of FIG. 11, hatching related to the magnitude of the deviation calculated by the measurement device 16 is illustrated. Practically, the magnitude of the deviation may be displayed in different colors. The region R1 is a region of channels each having a region deviation equal to or more than 1.5 times the standard deviation. The region R1 is set as a measurement candidate region. The region R2 is a region of channels each having a region deviation equal to or more than 0.5 times the standard deviation. The region R3 is a region of channels in which the region deviation of the calculation region is less than 0.5 times the standard deviation and the sum of the amplitudes inside the calculation region is larger than 0. The region R3 corresponds to the range of the detected human body. For example, the outer edge portion of the region R3 may be displayed with different hatching or colors, and the range of the detected human body may be clearly indicated. For example, the heat map in FIG. 11 may be displayed on a screen of a terminal device (not illustrated). For example, the subject wearing the optical sensor 10 can adjust the position to wear the optical sensor 10 by referring to the heat map displayed on the screen.

Figure 12:
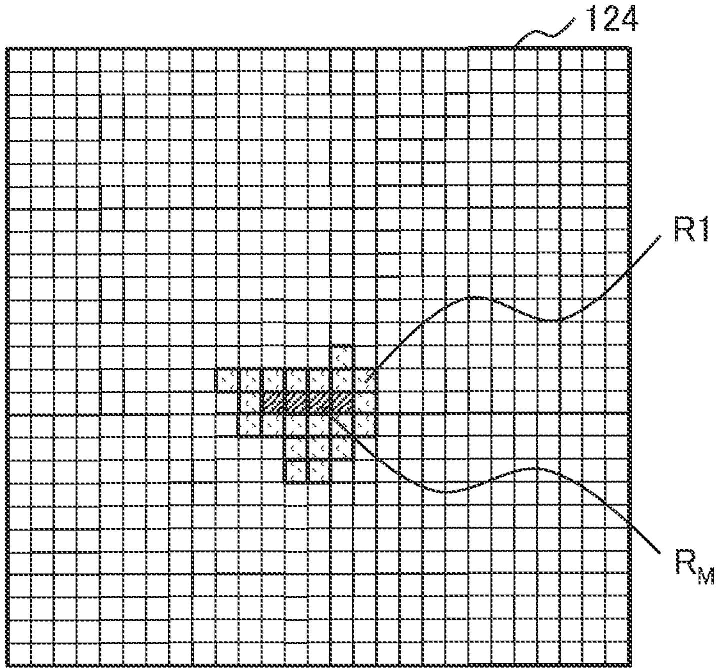
FIG. 12 is a conceptual diagram for describing an example of a measurement channel selected by the measurement device included in the biological data measurement system according to the first example embodiment.

FIG. 12 is a conceptual diagram for describing an example of the measurement region $R_M$ selected from the region R1 set as the measurement candidate region. FIG. 12 is a pixel image 124 related to the light receiving face of the light receiving element array 12. The measurement region $R_M$ is selected from channels within the range of the region R1 set as the measurement candidate region. As illustrated in FIG. 12, the number of measurement channels included in the measurement region $R_M$ is significantly smaller than the total number of channels included in the pixel image 124. Therefore, according to the present example embodiment, it is possible to greatly reduce the load applied to the reception of the reception signal, the communication of the reception signal, the calculation of the biological data, and the like in the measurement of the biological data.

The biological data output unit 166 acquires the biological data according to the second measurement instruction from the biological data generation unit 163. The biological data output unit 166 outputs the acquired biological data. For example, the biological data output unit 166 outputs a representative value of the biological data generated based on the received light signals received by the plurality of light receiving elements as the biological data. For example, the biological data output unit 166 outputs an average value of the biological data generated based on the received light signals received by the plurality of light receiving elements as the biological data. The biological data output unit 166 may output the biological data via a wire such as a cable or may output the biological data via wireless communication. For example, the biological data output unit 166 is configured to output the biological data via a wireless communication function (not illustrated) conforming to a standard such as Bluetooth (registered trademark) or WiFi (registered trademark). The communication function of the biological data output unit 166 may conform to a standard other than Bluetooth (registered trademark) or WiFi (registered trademark). The output destination and application of the biological data are not particularly limited. For example, the biological data output unit 166 outputs the biological data to a dedicated terminal device (not illustrated) having a screen. For example, the biological data output unit 166 outputs the biological data to a portable terminal (not illustrated) such as a smartphone or a tablet carried by the user. For example, the biological data output unit 166 outputs the biological data to an external system (not illustrated) constructed in a server or a cloud.

Figure 13:
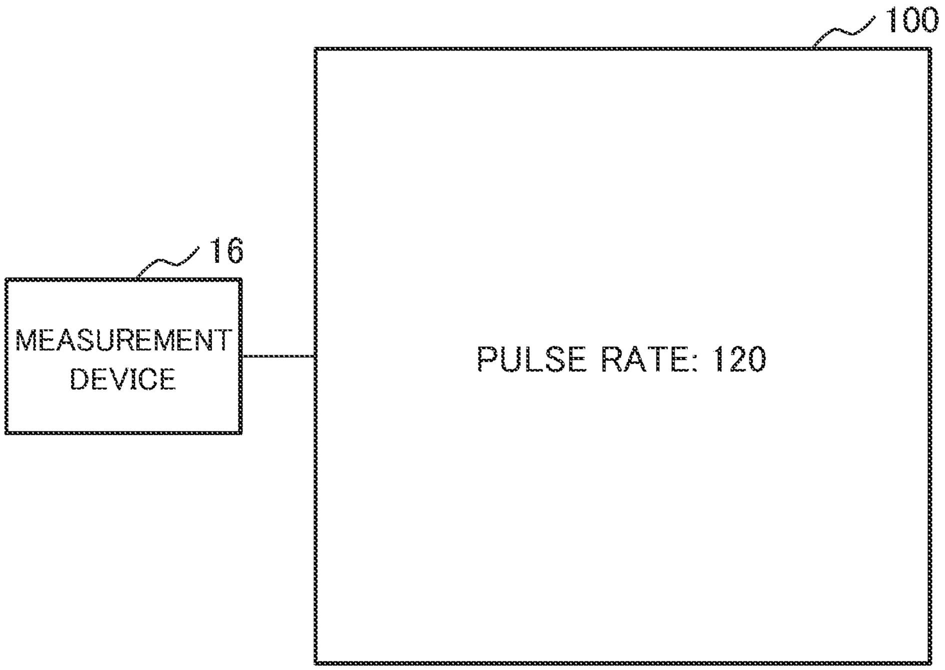
FIG. 13 is a conceptual diagram illustrating an example of displaying biological data (pulse rate) measured by the measurement device included in the biological data measurement system according to the first example embodiment on a screen.
Figure 14:
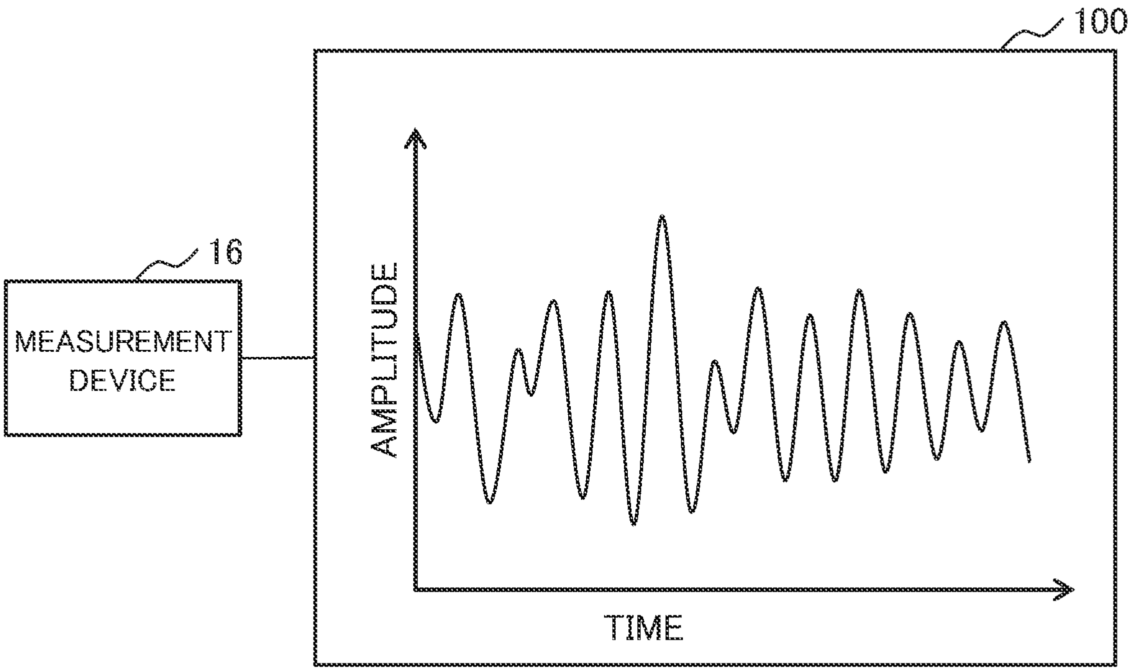
FIG. 14 is a conceptual diagram illustrating an example in which time series data of biological data measured by the measurement device included in the biological data measurement system according to the first example embodiment is displayed on a screen.

FIG. 13 illustrates an example in which the pulse rate measured according to the biological data output from the measurement device 16 is displayed on the screen of a terminal device 100. The pulse rate corresponds to the number of pulsation (pulse) per unit time. The number of pulsations per minute is defined as a pulse rate. The user who has visually recognized the pulse rate displayed on the screen can confirm the pulse rate of the subject. For example, the physical condition or the like of the subject can be verified according to the pulse rate. The pulse is derived from the heartbeat of the heart. Therefore, the pulse rate corresponds to the heart rate. When the pulse rate of the subject can be measured/displayed in real time, the physical condition of the subject can be accurately monitored in real time. For example, the subjective exercise intensity of the subject can be quantified according to the values of the exercise heart rate and the resting heart rate. The quantified subjective exercise intensity or the fatigue level according to the subjective exercise intensity may be displayed on the screen of the terminal device 100.

FIG. 10 illustrates an example in which the waveform of the time series data of the biological data (pulse) output from the measurement device 16 is displayed on the screen of the terminal device 100. The measurement device 16 generates the biological data using a reception signal received by a measurement channel having a large region deviation. Therefore, the waveform of the time series data of the biological data (pulse) output from the measurement device 16 is smooth with less drift and noise as illustrated in FIG. 10. The user who visually recognizes the waveform displayed on the screen can confirm the state of the pulse of the subject. For example, the state of the subject's body, health, mind, emotion, and the like can be verified based on the intensity, the interval, and the change over time of the pulse.

(Operation)

Next, an operation of the biological data measurement system 1 of the present example embodiment will be described with reference to the drawings. Hereinafter, the optical sensor 10 and the measurement device 16 constituting the biological data measurement system 1 will be individually described.

[Measurement Device]

Figure 15:
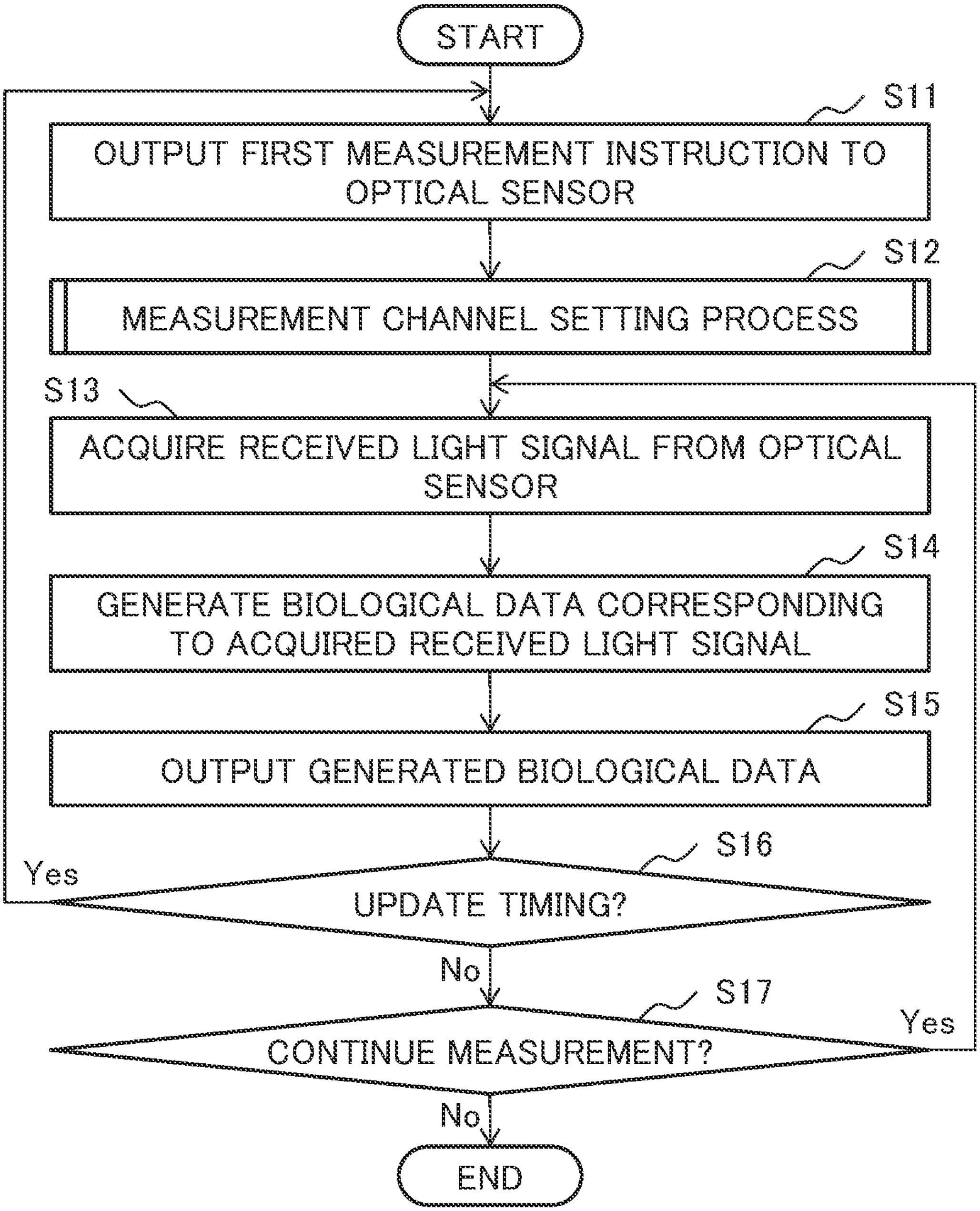
FIG. 15 is a flowchart for describing an example of the operation of the measurement device included in the biological data measurement system according to the first example embodiment.

FIG. 15 is a flowchart for describing an example of the operation of the measurement device 16. In the process along the flowchart of FIG. 15, the measurement device 16 will be described as an operation subject.

In FIG. 15, first, measurement device 16 outputs the first measurement instruction to optical sensor 10 (step S11).

Next, the measurement device 16 executes a measurement channel setting process (step S12). The measurement channel setting process is a process of setting a channel to be used for the main measurement according to the value of the biological data based on the reception signal received in response to the first measurement instruction. Details of the measurement channel setting process will be described later.

Next, the measurement device 16 acquires a received light signal from the optical sensor 10 (step S13). The reception signal acquired from the optical sensor 10 at this stage is a signal measured in main measurement according to the second measurement instruction.

Next, the measurement device 16 generates biological data according to the acquired received light signal (step S14).

Next, the measurement device 16 outputs the generated biological data (step S15).

In the case of the update timing of the measurement channel (Yes in step S16), the process returns to step S11. At the update timing, the measurement device 16 may output, to the optical sensor 10, a first measurement instruction to execute the first measurement process by narrowing a region to the region including the measurement channel.

After step S15, in a case where it is not the update timing of the measurement channel (No in step S16), when the measurement is continued (Yes in step S17), the process returns to step S13. On the other hand, in a case where the measurement is ended (No in step S17), the process along the flowchart of FIG. 15 is ended. The continuation/end of the measurement may be determined according to a preset timing, a timing at which the measurement value is no longer measured, or the like.

<Measurement Channel Setting Process for Each Channel>

Figure 16:
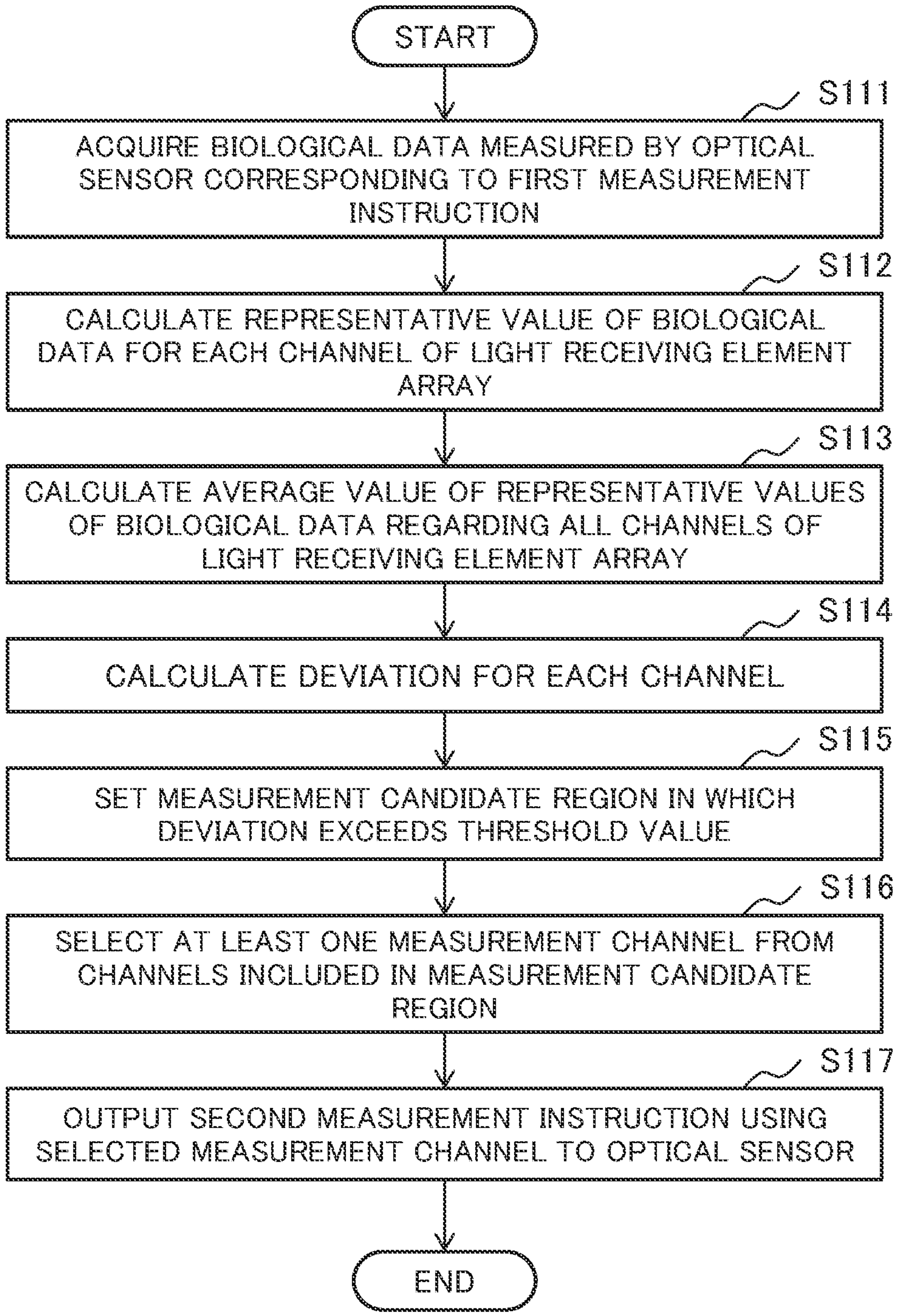
FIG. 16 is a flowchart for describing an example of a measurement channel setting process by the measurement device included in the biological data measurement system according to the first example embodiment.

Next, the measurement channel setting process for each channel by the measurement device 16 will be described with reference to the drawings. FIG. 16 is a flowchart for describing the measurement channel setting process for each channel.

In FIG. 16, first, the measurement device 16 acquires biological data measured by the optical sensor 10 according to the first measurement instruction (step S111).

Next, the measurement device 16 calculates a representative value of the biological data for each channel of the light receiving element array 12 (step S112). For example, the measurement device 16 calculates the maximum value of the biological data for each channel.

Next, the measurement device 16 calculates an average value of representative values of the biological data regarding all the channels of the light receiving element array 12 (step S113).

Next, the measurement device 16 calculates the channel deviation for each channel by subtracting the average value of the representative values of the biological data for all the channels from the representative value of the biological data for each channel constituting the light receiving element array 12 (step S114).

Next, the measurement device 16 sets a measurement candidate region in which the deviation exceeds a threshold value (step S115).

Next, the measurement device 16 selects at least one measurement channel from the channels included in the measurement candidate region (step S116). In other words, the measurement device 16 sets the measurement region within the range of the measurement candidate region.

Next, the measurement device 16 outputs a second measurement instruction using the selected measurement channel to the optical sensor 10 (step S117).

<Measurement Channel Setting Process for Each Calculation Region>

Figure 17:
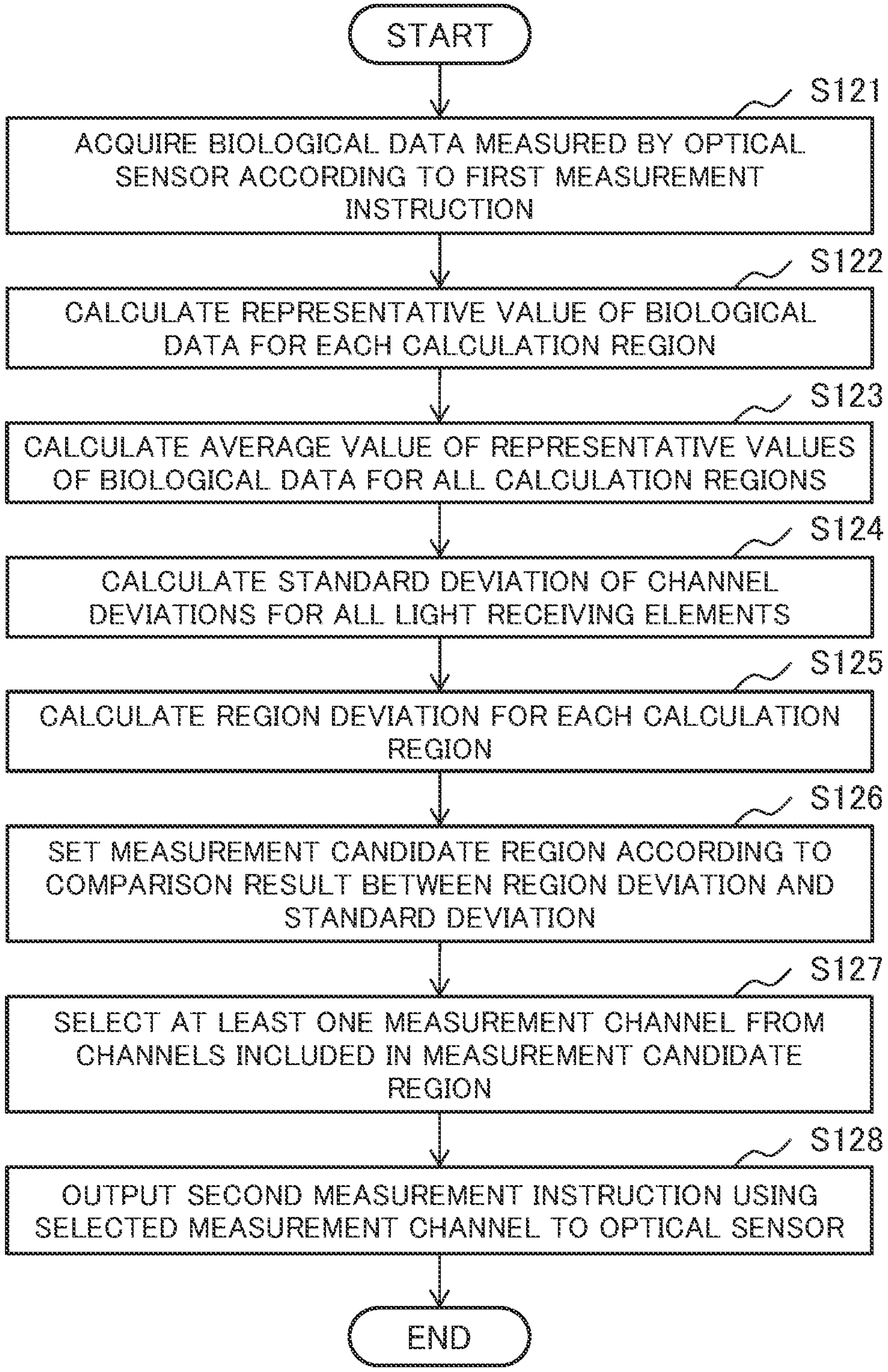
FIG. 17 is a flowchart for describing another example of a measurement channel setting process by the measurement device included in the biological data measurement system according to the first example embodiment.

Next, the measurement channel setting process for each calculation region by the measurement device 16 will be described with reference to the drawings. FIG. 17 is a flowchart for describing a measurement channel setting process for each calculation region.

In FIG. 17, first, the measurement device 16 acquires biological data measured by the optical sensor 10 according to the first measurement instruction (step S121).

Next, the measurement device 16 calculates a representative value of the biological data for each calculation region of the light receiving element array 12 (step S122). For example, the measurement device 16 calculates the maximum value of the biological data for each calculation region.

Next, the measurement device 16 calculates an average value of representative values of the biological data regarding all the calculation regions of the light receiving element array 12 (step S123).

Next, the measurement device 16 calculates the standard deviation of the channel deviations of all the light receiving elements (step S124).

Next, the measurement device 16 calculates the region deviation for each calculation region by subtracting the average value of the representative values of the biological data for all the calculation regions from the representative value of the biological data for each calculation region set in the light receiving element array 12 (step S125).

Next, the measurement device 16 sets the measurement candidate region according to the comparison result between the region deviation and the standard deviation (step S126). For example, the measurement device 16 selects, as the measurement candidate region, a selection region whose region deviation is equal to or more than 1.5 times the standard deviation.

Next, the measurement device 16 selects at least one measurement channel from the channels included in the measurement candidate region (step S127). In other words, the measurement device 16 sets the measurement region within the range of the measurement candidate region.

Next, the measurement device 16 outputs a second measurement instruction using the selected measurement channel to the optical sensor 10 (step S128).

[Optical Sensor]

Figure 18:
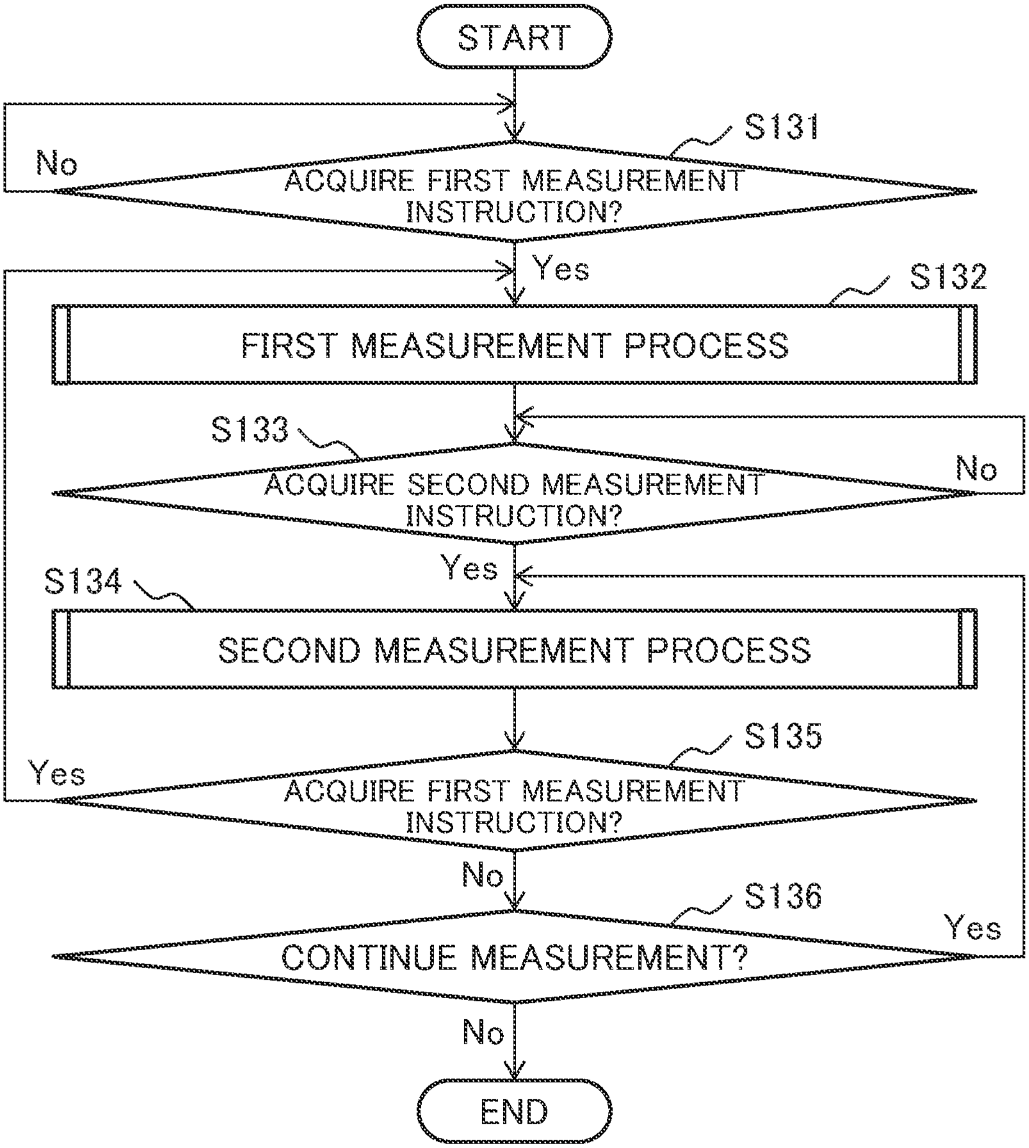
FIG. 18 is a flowchart for describing an example of the operation of the optical sensor included in the biological data measurement system according to the first example embodiment.

FIG. 18 is a flowchart for describing an example of the operation of the optical sensor 10. In the process along the flowchart of FIG. 18, the optical sensor 10 will be described as an operation subject.

In FIG. 18, when acquiring the first measurement instruction (Yes in step S131), the optical sensor 10 executes the first measurement process (step S132). Details of the first measurement process will be described later. On the other hand, when the first measurement instruction has not been acquired (No in step S131), the optical sensor 10 waits until the first measurement instruction is acquired.

After step S132, when the second measurement instruction is acquired (Yes in step S133), the optical sensor 10 executes the second measurement process (step S134). Details of the second measurement process will be described later. On the other hand, when the second measurement instruction is not acquired (No in step S133), the optical sensor 10 waits until the second measurement instruction is acquired.

After step S134, when the first measurement instruction is acquired (Yes in step S135), the optical sensor 10 returns the process to step S132 to execute the first measurement process. On the other hand, in a case where the first measurement instruction is not acquired (No in step S135), when the measurement is continued (Yes in step S136), the process returns to step S134 and the second measurement process is continued. On the other hand, in a case where the measurement is ended (No in step S136), the process along the flowchart of FIG. 18 is ended. The continuation/end of the measurement may be determined according to a preset timing, a timing at which the measurement value is no longer measured, or the like.

<First Measurement Process>

Figure 19:
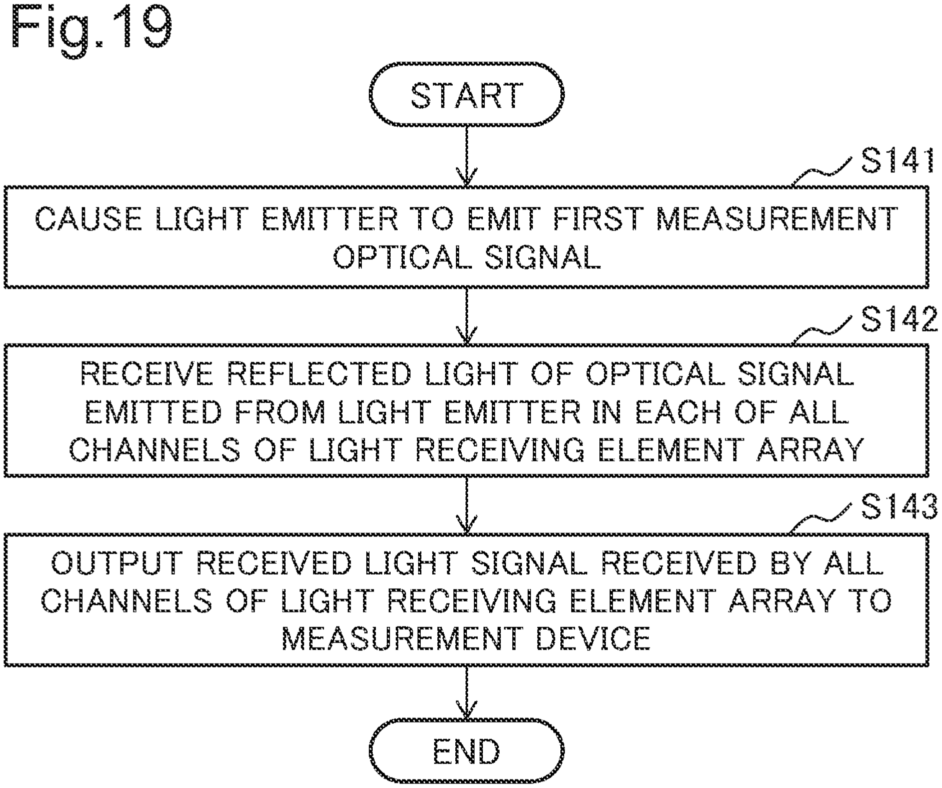
FIG. 19 is a flowchart for describing an example of a first measurement process by the optical sensor included in the biological data measurement system according to the first example embodiment.

Next, the first measurement process by the optical sensor 10 will be described with reference to the drawings. The first measurement process is executed in response to a first measurement instruction from the measurement device 16. FIG. 19 is a flowchart for describing the first measurement process by the optical sensor 10.

In FIG. 19, the optical sensor 10 causes the light emitter 11 to emit the first measurement optical signal (step S141).

Next, the optical sensor 10 receives the reflected light of the optical signal emitted from the light emitter 11 in each of all the channels of the light receiving element array 12 (step S142).

Next, the optical sensor 10 outputs the received light signal received by each of all the channels of the light receiving element array 12 to the measurement device 16 (step S143).

<Second Measurement Process>

Figure 20:
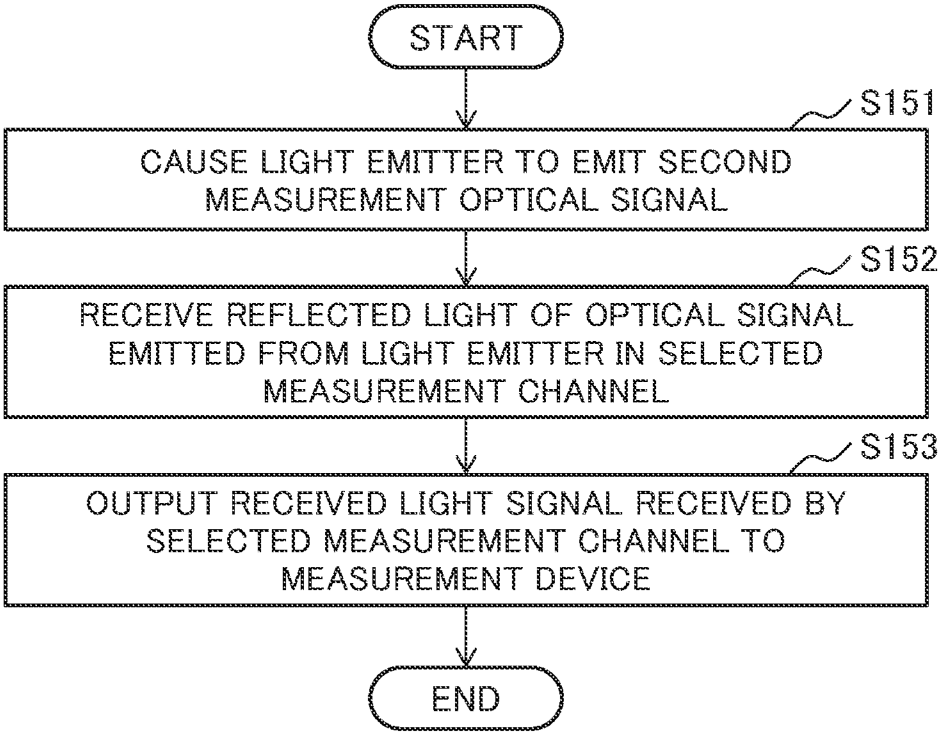
FIG. 20 is a flowchart for describing an example of a second measurement process by the optical sensor included in the biological data measurement system according to the first example embodiment.

Next, the second measurement process by the optical sensor 10 will be described with reference to the drawings. The second measurement process is executed in response to a second measurement instruction from the measurement device 16. FIG. 20 is a flowchart for describing the second measurement process by the optical sensor 10.

In FIG. 20, the optical sensor 10 causes light emitter 11 to emit the second measurement optical signal (step S151).

Next, the optical sensor 10 receives the reflected light of the optical signal emitted from the light emitter 11 by a measurement channel selected from the light receiving element array 12 (step S152).

Next, the optical sensor 10 outputs the received light signal received by the measurement channel selected from the light receiving element array 12 to the measurement device 16 (step S153).

As described above, the biological data measurement system of the present example embodiment includes the optical sensor and the measurement device. The optical sensor includes the plurality of light emitters, the light receiving element array, and the control unit. The plurality of light emitters is disposed on a measurement face of a substrate attached to the skin of a subject to be measured for biological data. The plurality of light emitters emits optical signals toward the skin of the subject. The light receiving element array includes a plurality of light receiving elements disposed two-dimensionally. The light receiving element array is disposed on the measurement face of the substrate. The light receiving element array receives reflected light of optical signals emitted from the plurality of light emitters. The control unit causes the plurality of light emitters to emit optical signals in response to a measurement instruction from the measurement device. The control unit receives a reception signal for each light receiving element according to reflected light of an optical signal received by each of the plurality of light receiving elements constituting the light receiving element array. The control unit outputs the received reception signal for each light receiving element to the measurement device. The control unit outputs the reception signal by the light receiving element within the range of the measurement region set by the measurement device to the measurement device in the second measurement period according to the second measurement instruction from the measurement device.

The measurement device of the present example embodiment includes a measurement instruction output unit, a reception signal acquisition unit, a biological data generation unit, a calculation unit, a measurement region setting unit, and a biological data output unit. The measurement instruction output unit outputs a measurement instruction including a first measurement instruction to instruct first measurement corresponding to preliminary measurement and a second measurement instruction to instruct second measurement corresponding to main measurement to an optical sensor including a light receiving element array in which a plurality of light receiving elements is two-dimensionally disposed. The reception signal acquisition unit acquires a reception signal of at least one of the plurality of light receiving elements according to the measurement instruction. The biological data generation unit generates biological data for each light receiving element using the acquired reception signal. The calculation unit calculates the deviation of the biological data for each light receiving element using the biological data generated using the reception signal acquired according to the first measurement instruction. The measurement region setting unit sets the measurement region including the light receiving element used for the second measurement according to the second measurement instruction according to the deviation of the biological data for each light receiving element. The biological data output unit outputs the biological data measured in the second measurement according to the second measurement instruction.

In the present example embodiment, in the measurement of the biological data using the optical sensor, the measurement region including the light receiving element used for the second measurement corresponding to the main measurement is set according to the deviation of the biological data for each light receiving element. According to the present example embodiment, in the second measurement corresponding to the main measurement, it is possible to reduce the load of measurement and communication by the optical sensor. Therefore, according to the present example embodiment, it is possible to constantly measure biological data using the optical sensor.

In an aspect of the present example embodiment, the measurement instruction output unit outputs, to the optical sensor, a first measurement instruction to instruct measurement using all of the plurality of light receiving elements constituting the light receiving element array. The measurement instruction output unit outputs, to the optical sensor, a second measurement instruction to instruct measurement using a light receiving element within a range of the measurement region among the plurality of light receiving elements constituting the light receiving element array. In the present aspect, in the first measurement corresponding to the preliminary measurement, the deviation of the biological data for each light receiving element is verified for all of the plurality of light receiving elements. Therefore, according to the present aspect, the optimum measurement region can be set on the light receiving face of the light receiving element array without missing. According to the present aspect, the load in the second measurement can be reduced by narrowing down the light receiving element to be subjected to the second measurement.

In an aspect of the present example embodiment, the calculation unit calculates the difference between the representative value of the biological data for each light receiving element and the representative values of all the biological data of the plurality of light receiving elements as the deviation of the biological data for each light receiving element. The measurement region setting unit sets a measurement candidate region according to the deviation of the biological data for each light receiving element. The measurement region setting unit sets the measurement region within the range of the measurement candidate region. According to the present aspect, the load in the second measurement can be reliably reduced by setting the measurement region within the range of the measurement candidate region set according to the deviation of the biological data for each light receiving element.

In an aspect of the present example embodiment, the measurement region setting unit sets, as the measurement candidate region, a region including the light receiving element in which the deviation of the biological data for each light receiving element exceeds a predetermined threshold value. According to the present aspect, the measurement region can be clearly set according to the predetermined threshold value.

In an aspect of the present example embodiment, the calculation unit calculates the standard deviation of the deviations of the biological data regarding all of the plurality of light receiving elements. The measurement region setting unit sets, as a measurement candidate region, a region including a light receiving element in which the deviation is equal to or more than predetermined times the standard deviation. The calculation unit sets the measurement region within the range of the measurement candidate region. According to the present aspect, the measurement region can be clearly set according to the value of the deviation with respect to the standard deviation.

In an aspect of the present example embodiment, the calculation unit calculates a difference between the representative value of the biological data for each of the plurality of calculation regions including the plurality of light receiving elements and the average value of the representative values of the biological data for all of the plurality of calculation regions as the region deviation of the biological data for each calculation region. The measurement region setting unit sets the measurement candidate region according to the region deviation of the biological data for each calculation region. According to the present aspect, by setting the measurement region according to the region deviation of the biological data for each calculation region, it is possible to reduce the load on the setting of the measurement region according to the first measurement.

In an aspect of the present example embodiment, the measurement instruction output unit outputs the first measurement instruction to the optical sensor at a timing when a predetermined period has elapsed since the second measurement according to the second measurement instruction was started, and updates the measurement region. According to the present aspect, continuous measurement of biological data can be implemented by updating the measurement region with good timing.

In an aspect of the present example embodiment, when the measurement value of the biological data falls below the reference value in the second measurement according to the second measurement instruction, the measurement instruction output unit outputs the first measurement instruction to the optical sensor to update the measurement region. According to the present aspect, continuous measurement of biological data can be implemented by updating the measurement region according to the measurement value of the biological data.

In an aspect of the present example embodiment, when updating the measurement region, the measurement instruction output unit outputs, to the optical sensor, a first measurement instruction including an instruction to perform the first measurement by narrowing a region to a peripheral region of the measurement region and the measurement region. According to the present aspect, the load applied to the first measurement can be reduced by narrowing the measurement range in the first measurement in updating the measurement region.

In an aspect of the present example embodiment, when the measurement value of the biological data is interrupted in the second measurement according to the second measurement instruction, the measurement region setting unit resets a region having a high rank of the deviation as the measurement region. The measurement instruction output unit outputs the second measurement instruction including an instruction to continue measurement in the reset measurement region to the optical sensor. According to the present aspect, continuous measurement of the biological data can be implemented by resetting the measurement region in a situation where the measurement value of the biological data is interrupted.

In an aspect of the present example embodiment, the biological data output unit outputs a heat map in which the measurement region is highlighted in association with the light receiving face of the light receiving element array. According to the present aspect, for example, by displaying the heat map on the screen, a person who has visually recognized the screen can confirm that an appropriate measurement region is set.

Second Example Embodiment

Next, an optical sensor according to a second example embodiment will be described with reference to the drawings. The optical sensor of the present example embodiment includes the function of the measurement device of the first example embodiment.

Figure 21:
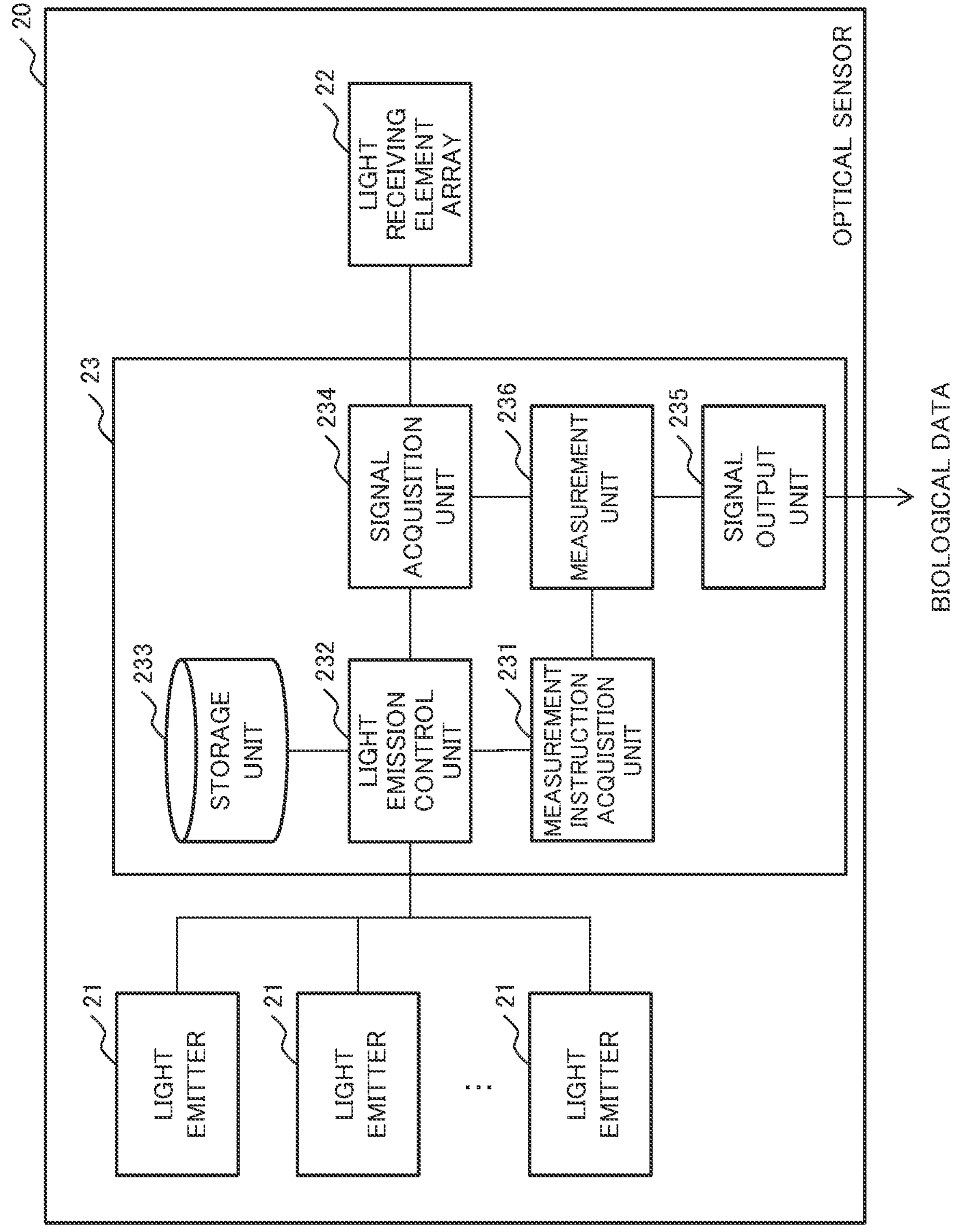
FIG. 21 is a block diagram illustrating an example of a configuration of an optical sensor according to a second example embodiment.

FIG. 21 is a block diagram illustrating an example of a configuration of an optical sensor 20 of the present example embodiment. The optical sensor 20 includes a plurality of light emitters 21, a light receiving element array 22, and a control unit 23. The plurality of light emitters 21, the light receiving element array 22, and the control unit 23 are disposed on the substrate as in the first example embodiment (FIGS. 2 to 3). Since the substrate is similar to the substrate 110 of the first example embodiment, a detailed description thereof will be omitted. Description of an adhesive layer or the like for attaching the optical sensor 20 to the human body is omitted.

The light emitter 21 has a configuration similar to that of the light emitter 11 of the first example embodiment. The light emitter 21 has an emission face that emits light used for measuring pulse. The plurality of light emitters 21 is disposed with their emission faces having the same direction. The emission faces of the plurality of light emitters 21 and the light receiving face of the light receiving element array 22 are disposed in the same direction. The emission face of the light emitter 21 faces the skin of the subject in a state where the optical sensor 20 is attached to the skin of the subject. The light emitter 21 emits an optical signal of a wavelength band in which a pulse can be measured according to the control of the control unit 23.

The light receiving element array 22 has a configuration similar to that of the light receiving element array 12 of the first example embodiment.

The light receiving element array 22 has a light receiving face that receives reflected light of the optical signal emitted from the light emitter 21. The reflected light is a light component that is reflected/scattered under the skin (inside the body) of the subject and reaches the light receiving face of the light receiving element array 22 in the optical signal emitted from the light emitter 21. On the light receiving face of the light receiving element array 22, a plurality of light receiving elements is disposed in a two-dimensional array. The light intensity of the reflected light received by each of the plurality of light receiving elements disposed in a two-dimensional array is measured in association with the positions (addresses) of the light receiving elements.

The control unit 23 has a configuration similar to that of the control unit 13 of the first example embodiment. The control unit 23 is different from the control unit 13 of the first example embodiment in that it includes the function of the measurement device 16 of the first example embodiment. The control unit 23 controls the plurality of light emitters 21. For example, the control unit 23 is achieved by a microcomputer or a microcontroller.

As illustrated in FIG. 21, the control unit 23 includes a measurement instruction acquisition unit 231, a light emission control unit 232, a storage unit 233, a signal acquisition unit 234, a signal output unit 235, and a measurement unit 236. Hereinafter, the function of the measurement device 16 of the first example embodiment will be described as being exerted by the measurement unit 236. The function of the measurement unit 236 may be divided into a plurality of configurations.

The measurement unit 236 has a function similar to that of the measurement device 16 of the first example embodiment. When the optical sensor 10 is activated, the measurement unit 236 outputs a first measurement instruction to perform preliminary measurement to the light emission control unit 232 prior to the continuous main measurement. The first measurement instruction is an instruction to perform preliminary measurement for a certain period in all the light receiving elements of the light receiving element array 22. The measurement unit 236 outputs a second measurement instruction to perform measurement in the selected measurement channel to the optical sensor 20. The second measurement instruction is an instruction to perform continuous main measurement in a selected measurement channel among the light receiving elements of the light receiving element array 22.

The measurement unit 236 outputs a first measurement instruction to the light emission control unit 232 in order to update the measurement channel at a predetermined update timing. For example, the measurement unit 236 may output an instruction to perform the first measurement instruction to the light emission control unit 232 with respect to the region including the measurement channel being measured. The measurement unit 236 may update the measurement channel according to the value or variation of the biological data during the main measurement.

The measurement unit 236 acquires a reception signal from the signal acquisition unit 234. The measurement unit 236 generates biological data using the acquired reception signal. For example, the measurement unit 236 generates pulse data using time series data of the acquired reception signal. The biological data generated by the measurement unit 236 is not particularly limited.

The measurement unit 236 selects a channel on which the main measurement is performed using the biological data based on the reception signal received in response to the first measurement instruction. The measurement unit 236 calculates a representative value of the amplitude of the biological data for each channel for all of the plurality of light receiving elements (channels) constituting the light receiving element array 22. The measurement unit 236 calculates an average value of representative values of the plurality of light receiving elements (channels) constituting the light receiving element array 22. The measurement unit 236 calculates, for each channel, a deviation (also referred to as a channel deviation) obtained by subtracting an average value of representative values of a plurality of light receiving elements (channels) from a representative value of each light receiving element (channel).

The measurement unit 236 may calculate the deviation of the measurement values of the plurality of light receiving elements (channels) constituting the light receiving element array 22 not for single channel but for the plurality of channels. For example, the measurement unit 236 may set a region (also referred to as a calculation region) including a plurality of light receiving elements and calculate a deviation of a measurement value for each calculation region. For example, the measurement unit 236 calculates a value obtained by subtracting the average value of the representative values of the plurality of light receiving elements (channels) from the average value of the representative values of the measurement values by the light receiving elements (channels) included in the calculation region as a deviation (also referred to as a region deviation) of the calculation region. The measurement unit 236 calculates a standard deviation of channel deviations calculated for a plurality of light receiving elements (channels).

The measurement unit 236 selects a channel (also referred to as a measurement channel) to be used for main measurement of the biological data based on the channel deviation calculated for each channel, the region deviation calculated for each calculation region, and the standard deviation of the channel deviations regarding the plurality of light receiving elements (channels). For example, the measurement unit 236 sets a region of a channel where a deviation such as a channel deviation or a region deviation exceeds a predetermined threshold value as a measurement candidate region. For example, the measurement unit 236 selects the measurement channel according to the comparison result between the deviation such as the channel deviation or the region deviation and the standard deviation of the channel deviations regarding the plurality of light receiving elements (channels). The measurement unit 236 sets, for the measurement candidate region, a light receiving element (channel) in which a deviation such as a channel deviation or a region deviation is equal to or more than predetermined times a standard deviation of the channel deviations related to a plurality of light receiving elements (channels). For example, the measurement unit 236 sets, for the measurement candidate region, a light receiving element (channel) in which a deviation such as a channel deviation or a region deviation is equal to or more than 1.5 times the standard deviation of the channel deviations related to the plurality of light receiving elements (channels). The measurement unit 236 selects a measurement channel from the light receiving elements (channels) set in the measurement candidate region. The measurement unit 236 sets the selected measurement channel for the measurement region.

The measurement unit 236 may store a measurement channel having a high rank of a channel deviation or a region deviation among channels included in the measurement candidate region. For example, in a case where the measurement in the measurement channel selected according to the channel deviation or the region deviation is interrupted, the measurement unit 236 reselects the measurement channel from the region having a high rank of the channel deviation. In other words, when the measurement in the measurement region is interrupted, the measurement unit 236 resets the region having a high rank of the channel deviation or the region deviation as the measurement region. In this way, even when the measurement in the measurement channel is suddenly interrupted, the measurement of the biological data can be continued. Such processing can also be applied to that of the first example embodiment.

The measurement instruction acquisition unit 231 has a configuration similar to that of the measurement instruction acquisition unit 131 of the first example embodiment. The measurement instruction acquisition unit 231 acquires the measurement instruction from the measurement unit 236. The measurement instruction acquisition unit 231 acquires an instruction to perform preliminary measurement (also referred to as a first measurement instruction) from the measurement unit 236. The measurement instruction acquisition unit 231 outputs the acquired first measurement instruction to the light emission control unit 232 and the signal acquisition unit 234. The measurement instruction acquisition unit 231 acquires an instruction to perform measurement in the measurement channel (also referred to as a second measurement instruction) from the measurement unit 236. The measurement instruction acquisition unit 231 outputs the acquired second measurement instruction to the light emission control unit 232 and the signal acquisition unit 234. The measurement instruction acquisition unit 231 may be omitted, and the measurement unit 236 may output the first measurement instruction or the second measurement instruction to the light emission control unit 232 and the signal acquisition unit 234.

The light emission control unit 232 has a configuration similar to that of the light emission control unit 132 of the first example embodiment. The light emission control unit 232 acquires a measurement instruction by the measurement unit 236 from the measurement instruction acquisition unit 231. The light emission control unit 232 acquires a first measurement instruction to perform preliminary measurement (first measurement process) from the measurement instruction acquisition unit 231. The light emission control unit 232 performs control to cause the plurality of light emitters 21 to emit light in response to the first measurement instruction. The light emission control unit 232 controls the plurality of light emitters 21 by a control method according to the first measurement instruction stored in the storage unit 233. The light emission control unit 232 acquires a second measurement instruction to perform continuous main measurement (second measurement process) from the measurement instruction acquisition unit 231. The light emission control unit 232 performs control to cause the plurality of light emitters 21 to emit light in response to the second measurement instruction. The light emission control unit 232 controls the plurality of light emitters 21 by a control method according to the second measurement instruction stored in the storage unit 233.

The storage unit 233 has a configuration similar to that of the storage unit 133 of the first example embodiment. The storage unit 233 stores a control method for causing the plurality of light emitters 21 to emit light. The control method stored in the storage unit 233 is referred to by the light emission control unit 232. The control method stored in the storage unit 233 is not particularly limited.

The signal acquisition unit 234 has a configuration similar to that of the signal acquisition unit 134 of the first example embodiment. The signal acquisition unit 234 acquires a measurement instruction by the measurement unit 236 from the measurement instruction acquisition unit 231. The signal acquisition unit 234 acquires the first measurement instruction to perform preliminary measurement (first measurement process) from the measurement instruction acquisition unit 231. In response to the first measurement instruction, the signal acquisition unit 234 acquires the received light signals received by each of all the light receiving elements constituting the light receiving element array 22. The signal acquisition unit 234 outputs the received light signals received by all the light receiving elements to the measurement unit 236. The signal acquisition unit 234 acquires a second measurement instruction to perform continuous main measurement (second measurement process) from the measurement instruction acquisition unit 231. In response to the second measurement instruction, the signal acquisition unit 234 acquires the received light signal received by the light receiving element set to the measurement channel selected by the measurement unit 236. The signal acquisition unit 234 outputs the received light signal received by the light receiving element set in the measurement channel to the measurement unit 236.

In response to the second measurement instruction, the measurement unit 236 generates the biological data using the received light signal acquired from the signal acquisition unit 234. The measurement unit 236 outputs the biological data measured according to the second measurement instruction to the signal output unit 235.

The signal output unit 235 acquires the biological data measured according to the second measurement instruction from the measurement unit 236. The signal output unit 235 outputs the acquired biological data. The signal output unit 235 may output the biological data via a wire such as a cable or may output the biological data via wireless communication. For example, the signal output unit 235 is configured to output biological data via a wireless communication function (not illustrated) conforming to a standard such as Bluetooth (registered trademark) or WiFi (registered trademark). The communication function of the signal output unit 235 may conform to a standard other than Bluetooth (registered trademark) or WiFi (registered trademark). The output destination and application of the biological data are not particularly limited. For example, the signal output unit 235 outputs the biological data to a dedicated terminal device (not illustrated) having a screen. For example, the signal output unit 235 outputs the biological data to a portable terminal (not illustrated) such as a smartphone or a tablet carried by the user. For example, the signal output unit 235 outputs the biological data to an external system (not illustrated) constructed in a server or a cloud. For example, the signal output unit 235 may store the biological data acquired from the measurement unit 236 in a storage device such as a flash memory and collectively output the biological data measured for a predetermined period.

(Operation)

Figure 22:
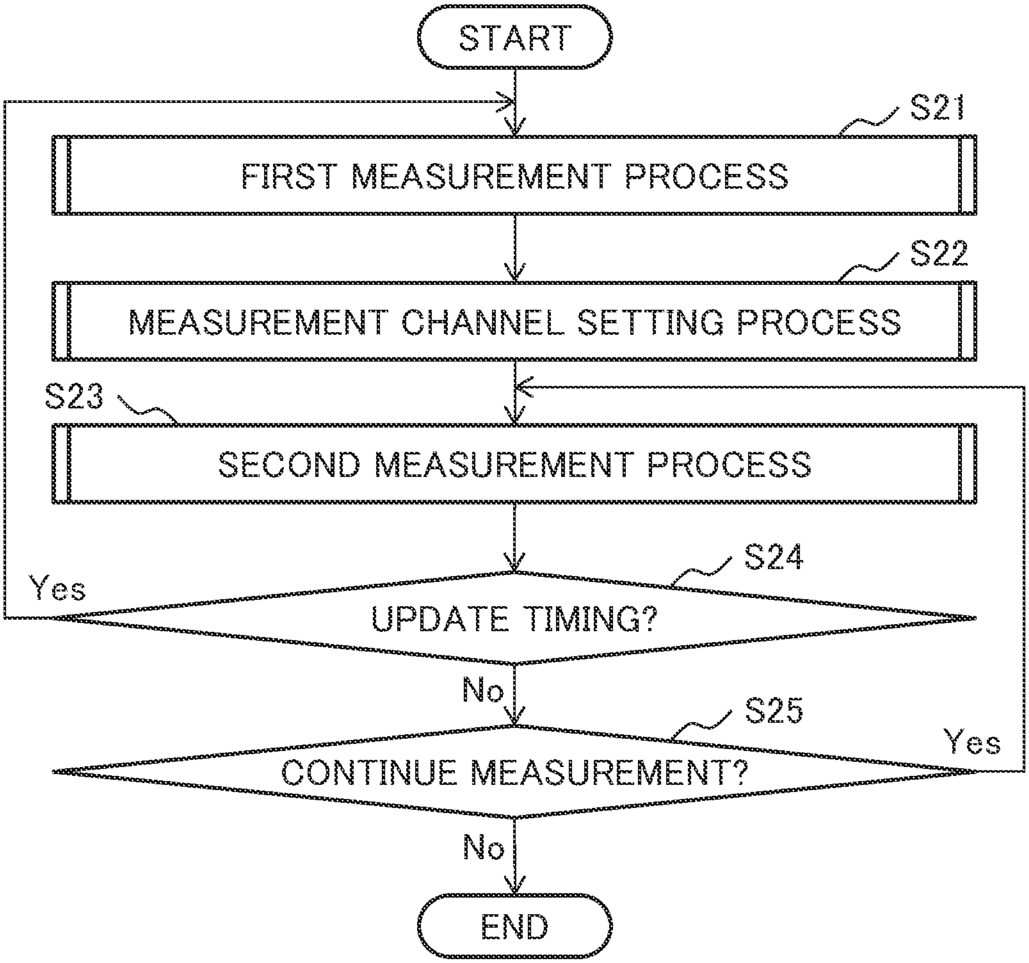
FIG. 22 is a flowchart for describing an example of an operation of the optical sensor according to the second example embodiment.

Next, an operation of the optical sensor 20 of the present example embodiment will be described with reference to the drawings. FIG. 22 is a flowchart for describing an example of the operation of the optical sensor 20. In the process along the flowchart of FIG. 22, the optical sensor 20 will be described as an operation subject.

In FIG. 22, first, when activated, the optical sensor 20 executes a first measurement process (step S21). Details of the first measurement process in step S21 are similar to those of the first measurement process in FIG. 19.

Next, the optical sensor 20 executes a measurement channel setting process (step S22). The measurement channel setting process in step S22 is similar to the measurement channel setting process in FIGS. 16 and 17.

Next, the optical sensor 20 executes a second measurement process (step S23). The second measurement process in step S23 is similar to the second measurement process in FIG. 20.

In the case of the update timing of the measurement channel (Yes in step S24), the process returns to step S21. At the update timing, the optical sensor 20 may perform the first measurement process by narrowing a region to the region including the measurement channel.

After step S23, in a case where it is not the update timing of the measurement channel (No in step S24), when the measurement is continued (Yes in step S25), the process returns to step S23. On the other hand, in a case where the measurement is ended (No in step S25), the process along the flowchart of FIG. 22 is ended. The continuation/end of the measurement may be determined according to a preset timing, a timing at which the measurement value is no longer measured, or the like.

As described above, the optical sensor of the present example embodiment includes the plurality of light emitters, the light receiving element array, and the control unit. The plurality of light emitters is disposed on a measurement face of a substrate to be attached to the skin of the subject whose biological data is to be measured. The plurality of light emitters emits optical signals toward the skin of the subject. The light receiving element array includes a plurality of light receiving elements disposed two-dimensionally. The light receiving element array is disposed on the measurement face of the substrate. The light receiving element array receives reflected light of optical signals emitted from the plurality of light emitters.

The control unit of the present example embodiment includes a measurement instruction acquisition unit, a light emission control unit, a storage unit, a signal acquisition unit, a measurement unit, and a signal output unit. The measurement unit outputs a measurement instruction including a first measurement instruction to instruct first measurement corresponding to preliminary measurement and a second measurement instruction to instruct second measurement corresponding to main measurement. The measurement instruction acquisition unit acquires a measurement instruction from the measurement unit. The light emission control unit causes the plurality of light emitters to emit optical signals in response to a measurement instruction from the measurement device. The signal acquisition unit acquires a reception signal for each light receiving element according to reflected light of an optical signal received by each of the plurality of light receiving elements constituting the light receiving element array. The measurement unit acquires a reception signal of at least one of the plurality of light receiving elements according to the measurement instruction. The measurement unit generates biological data for each light receiving element using the acquired reception signal. The measurement unit calculates a deviation of the biological data for each light receiving element using the biological data generated using the reception signal acquired according to the first measurement instruction. The measurement unit sets the measurement region including the light receiving element used for the second measurement according to the second measurement instruction according to the deviation of the biological data for each light receiving element. The signal output unit outputs the biological data measured in the second measurement according to the second measurement instruction.

The optical sensor of the present example embodiment sets the measurement region including the light receiving element used for the second measurement corresponding to the main measurement according to the deviation of the biological data for each light receiving element in the measurement of the biological data. According to the present example embodiment, in the optical sensor, a load of measurement and communication can be reduced, and it is possible to constantly measure biological data.

Third Example Embodiment

Next, a biological information estimation system according to a third example embodiment will be described with reference to the drawings. The biological information estimation system according to the present example embodiment estimates biological information about a subject based on biological data (pulse signal) output from the measurement device according to each of the first and second example embodiments.

(Configuration)

Figure 23:
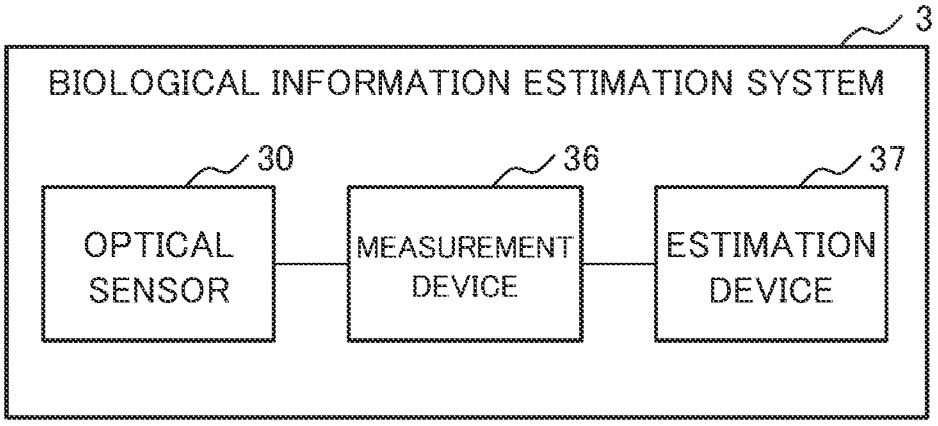
FIG. 23 is a block diagram illustrating an example of a configuration of a biological information estimation system according to a third example embodiment.

FIG. 23 is a block diagram illustrating an example of a configuration of a biological information estimation system 3 according to the present example embodiment. The biological information estimation system 3 includes an optical sensor 30, a measurement device 36, and an estimation device 37. The optical sensor 30 is the optical sensor 10 of the first example embodiment. The measurement device 36 is the measurement device 16 of the first example embodiment. Details of the optical sensor 30 and the measurement device 36 will not be described. The biological information estimation system 3 may include the optical sensor 20 of the second example embodiment. In a case where the biological information estimation system 3 includes the optical sensor 20 of the second example embodiment, the measurement device 36 can be omitted. The biological information estimation system 3 may include the measurement device 36 and the estimation device 37.

The estimation device 37 acquires the pulse signal output from the optical sensor 30. The estimation device 37 estimates biological information about the subject according to the acquired pulse signal. The biological information of the subject includes a pulse, a physical condition, an emotion, and the like.

For example, the estimation device 37 estimates the pulse of the subject based on the pulse signal. For example, the estimation device 37 estimates the pulse according to the interval of the maximum value/minimum value appearing in the time series data of the pulse signal. For example, the estimation device 37 estimates the pulse according to the expression cycle of the feature amount extracted from the time series data of the pulse signal. The estimation device 37 outputs information about the pulse such as the estimated pulse interval and the intensity of the pulse signal.

For example, the estimation device 37 estimates the physical condition of the subject based on the pulse signal. For example, the estimation device 37 estimates the physical condition of the subject based on the time series data of the pulse signal. When the subject is at rest, the intensity of the pulse signal decreases and the pulse interval increases. When the subject is exercising, the intensity of the pulse signal increases and the pulse interval decreases. When the subject has an irregular heartbeat, the pulse rhythm is irregular or the pulse is interrupted. The physical condition of the subject also affects the baseline of the time series data of the pulse signal. When the subject's physical condition is stable, the baseline variation is small. On the other hand, in a case where the physical condition of the subject is unstable, the fluctuation of the baseline increases. For example, the baseline shows a rising tendency or a falling tendency depending on the physical condition of the subject. In a case where the subject suffers from some disease, a characteristic peculiar to the disease may appear in the pulse signal. When an estimation model that is trained on a feature appearing in a pulse signal due to a disease in advance is used, it is possible to estimate a disease that the subject suffers according to the pulse signal of the subject. The estimation device 37 outputs information about the estimated physical condition of the subject.

For example, the physical condition such as stress, fatigue, and sleepiness held by the subject also affects the pulse signal. The estimation device 37 extracts a feature amount according to a physical condition such as stress, fatigue, and drowsiness from the pulse time series data. For example, the estimation device 37 extracts feature amounts such as an average value, a standard deviation, a coefficient of variation, a root mean square, and a frequency component of the pulse time series data from the pulse time series data. The estimation device 37 estimates the physical condition of the subject according to the extracted feature amount. The estimation device 37 outputs information about the estimated physical condition of the subject, recommendation information according to the estimated physical condition, and the like.

For example, the estimation device 37 estimates the emotion of the subject based on the pulse signal. The emotion of the subject can be estimated by the intensity or fluctuation of the pulse. For example, the estimation device 37 estimates the degree of emotions such as pleasure, anger, sorrow, and delight according to the fluctuation of the pulse time series data. For example, the estimation device 37 may estimate the emotion of the subject according to the variation in the baseline of the time series data related to the pulse. For example, as the "anger" of the subject gradually increases, an increasing tendency appears in the baseline according to an increase in the degree of excitement (awakeness level) of the subject. For example, as the "sorrow" of the subject gradually increases, a downward tendency appears in the baseline according to the decrease in the degree of excitement (awakeness level of the subject.

Figure 24:
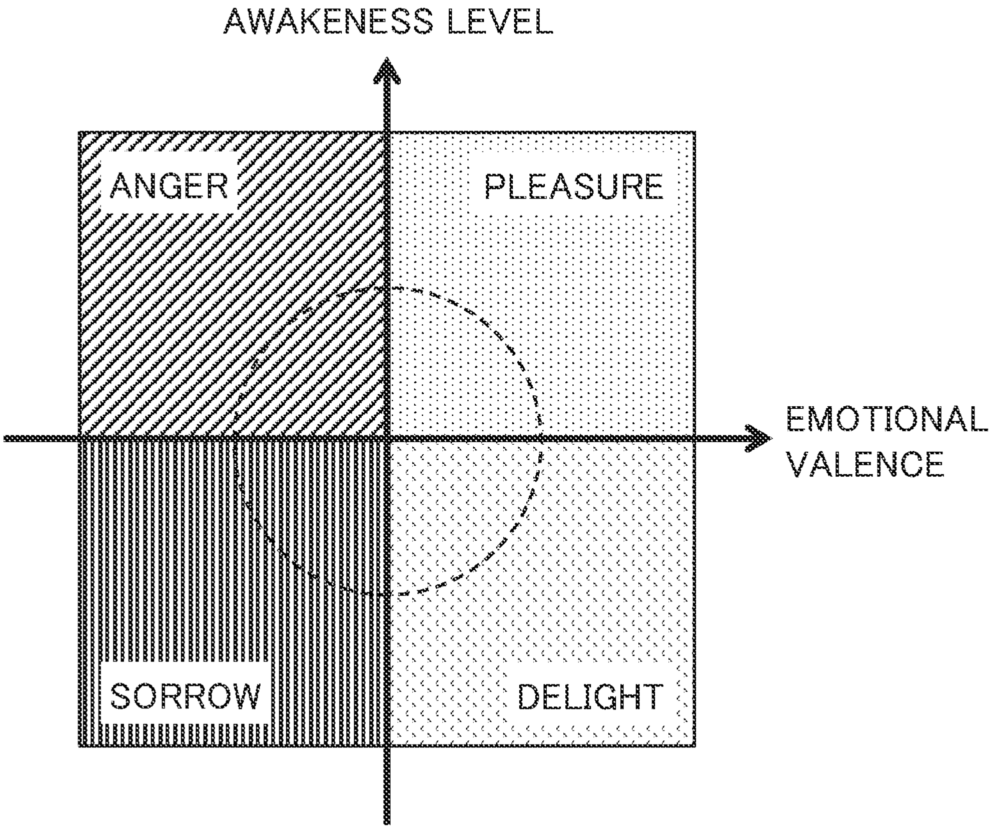
FIG. 24 is a conceptual diagram for describing an emotion estimated based on a pulse signal by the estimation device of the biological information estimation system according to the third example embodiment.

FIG. 24 is a conceptual diagram for describing emotions estimated by the estimation device 37 based on a pulse signal. In the example of FIG. 24, the emotion is estimated according to the relationship between the emotional valence (horizontal axis) and the awakeness level (vertical axis). The emotional valence (horizontal axis) quantifies emotional comfort. The emotional valence (horizontal axis) indicates a more comfortable state toward the right and a more uncomfortable state toward the left. The awakeness level (vertical axis) quantifies emotional arousal. The awakeness level (vertical axis) indicates a more excited state toward the top and a calmer state toward the bottom. In the example of FIG. 24, emotions of delight, anger, sorrow, and delight are associated with each quadrant defined by the emotional valence (horizontal axis) and the awakeness level (vertical axis). "Pleasure" is associated with the first quadrant. The greater the emotional valence and the greater the awakeness level, the greater the degree of "pleasure". The second quadrant is associated with "anger". The lower the emotional valence and the higher the awakeness level, the higher the degree of "anger". "Sorrow" is associated with the third quadrant. The lower the emotional valence and the lower the awakeness level, the higher the degree of "sorrow". "Delight" is associated with the fourth quadrant. The higher the emotional valence and the lower the awakeness level, the higher the degree of "delight". The association of emotions with respect to the graph of FIG. 24 is an example, and does not limit the criteria for emotion estimation by the biological information estimation system 3 of the present example embodiment. For example, the emotion of the subject is not classified into four emotion states such as delight, anger, sorrow, and delight, but may be classified into more detailed emotion states. The emotion of the subject may be classified not only by the two-dimensional coordinate system as illustrated in FIG. 24 but also by an any emotion state classification method.

The heart rate fluctuates under the influence of activity related to the autonomic nerve such as sympathetic nerve and parasympathetic nerve. Similarly, the pulse rate fluctuates under the influence of activity related to the autonomic nerve such as sympathetic nerve and parasympathetic nerve. For example, a low frequency component or a high frequency component can be extracted by frequency analysis of time series data of the pulse rate. The influence of the sympathetic nerve and the parasympathetic nerve is reflected in the low frequency component. The influence of the parasympathetic nerve is reflected in the high frequency component. Therefore, for example, the activity state of the autonomic nerve function can be estimated according to the ratio between the high frequency component and the low frequency component.

Sympathetic nerves tend to be active when the subject is excited. When the sympathetic nerve of the subject is active, pulsation is fast. That is, the greater the pulse rate, the greater the awakeness level. Parasympathetic nerves tend to be active when the subject is relaxed. When the subject relaxes, the pulsation is slow. That is, the smaller the pulse rate, the smaller the awakeness level. In this manner, the estimation device 37 can measure the awakeness level in accordance with the pulse rate. For example, the emotional valence can be evaluated according to the variation in the pulse interval. The more pleasant the emotion state, the more stable the emotion and the smaller the variation in the pulse interval. That is, the smaller the variation in the pulse interval, the larger the emotional valence. On the other hand, the more unpleasant the emotion state, the more unstable the emotion, and the larger the variation in the pulse interval. That is, the greater the variation in the pulse interval, the greater the emotional valence. In this manner, the estimation device 37 can measure the emotional valence according to the pulse interval. However, the method of measuring the awakeness level and the emotional valence is not limited to the methods and criteria described herein as long as the pulse signal output from the optical sensor 30 is used.

The estimation device 37 estimates the awakeness level and the emotional valence based on the time series data of the pulse signal. The estimation device 37 estimates the emotion according to the measured coordinates of the awakeness level and the emotional valence in the coordinate system of the graph of FIG. 24. When the coordinates of the awakeness level and the emotional valence measured for a certain subject are in the first quadrant, the estimation device 37 estimates that the emotion state of the subject is "pleasure". When the coordinates of the awakeness level and the emotional valence measured for a subject are in the second quadrant, the estimation device 37 estimates that the emotion state of the subject is "anger". When the coordinates of the awakeness level and the emotional valence measured for a certain subject are in the third quadrant, the estimation device 37 estimates that the emotion state of the subject is "sorrow". When the coordinates of the awakeness level and the emotional valence measured for a certain subject are in the fourth quadrant, the estimation device 37 estimates that the emotion state of the subject is "delight". For example, in a case where the emotional valence and the awakeness level do not exceed the threshold value, the estimation device 37 determines that the emotion state of the subject is a normal state. For example, if the coordinates of the emotional valence and the awakeness level are inside a circle of a broken line shown at the center of the coordinate system in FIG. 24, the estimation device 37 determines that the emotion state of the subject is a normal state. The threshold value for determining that the emotion state of the subject is a normal state can be set to any value. For example, such a threshold value may be different for each emotion of delight, anger, sorrow, and delight.

Figure 25:
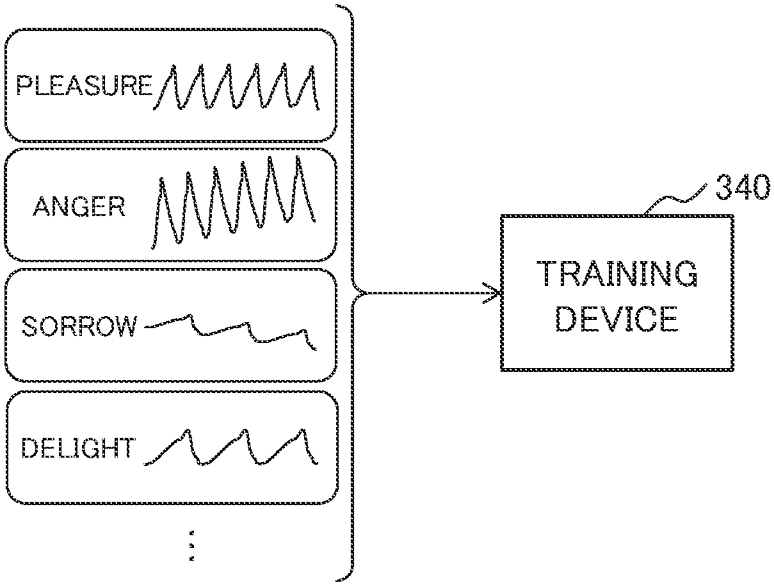
FIG. 25 is a conceptual diagram for describing an example of training for generating an estimation model used for emotion estimation by an estimation device of the biological information estimation system according to the third example embodiment.

The estimation device 37 may be configured to estimate an emotion using a machine training method. FIG. 25 is a conceptual diagram illustrating an example of a training device 340 with which a data set of a feature amount (explanatory variable) extracted from a pulse signal and an emotion (response variable) is trained as teacher data. The teacher data is data in which the label of the emotion state at that time is given to the feature amount extracted from the pulse signal measured for the subject in any of the emotion states of delight, anger, sorrow, and delight. The teacher data may be data in which a label of the emotion state at that time is given to a pulse signal measured for a subject in any emotion state of pleasure, anger, sorrow, and delight. The training device 340 generates an estimation model by supervised learning using teacher data. For example, the estimation model 370 is generated in advance by the training device 340 trained with teacher data related to a plurality of subjects. The estimation model 370 outputs the estimation result of the emotion of the subject according to the input of the feature amount extracted from the pulse signal. A specific method of machine training is not particularly limited.

Figure 26:
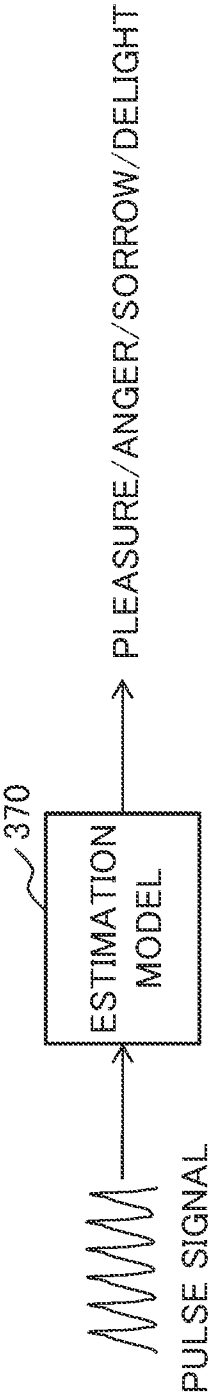
FIG. 26 is a conceptual diagram for describing an example of emotion estimation by an estimation device of the biological information estimation system according to the third example embodiment.

FIG. 26 is a conceptual diagram for describing an example in which the estimation device 37 estimates an emotion using the estimation model 370. In the example of FIG. 26, the estimation result of any emotion of delight, anger, sorrow, and delight is output from the estimation model 370 according to the input of the pulse signal of the subject. For example, the information about the estimation result of the emotion output from the estimation model 370 is displayed on a screen of a terminal device or the like (not illustrated).

Figure 27:
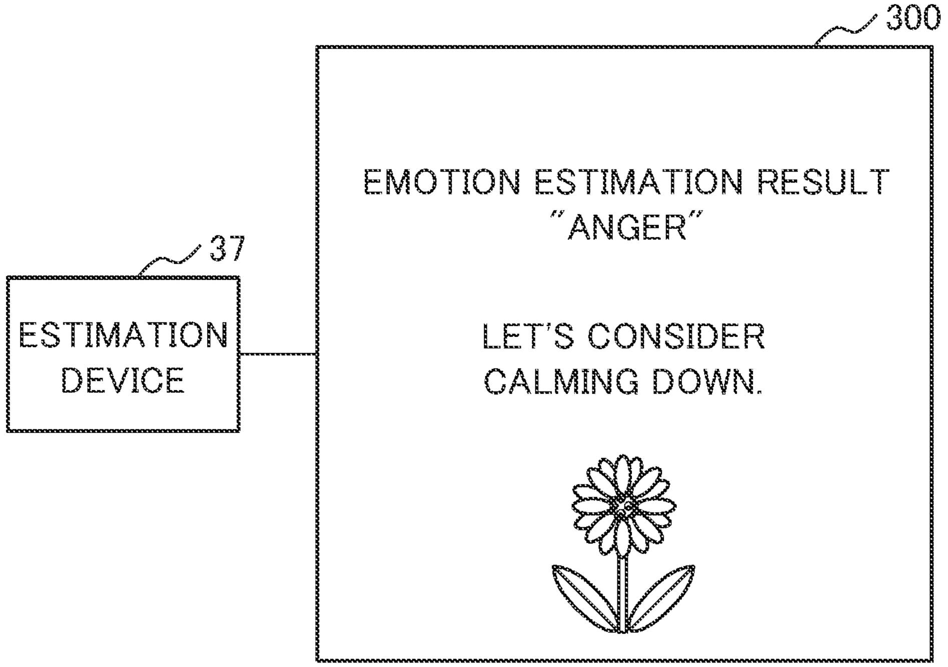
FIG. 27 is a conceptual diagram illustrating an example in which information about a subject's emotion estimated by an estimation device of the biological information estimation system according to the third example embodiment is displayed on a screen of a terminal device.

FIG. 27 illustrates an example in which the information about the emotion of the subject estimated by the estimation device 37 is displayed on the screen of a terminal device 300 according to the pulse signal output from the optical sensor 30. In the example of FIG. 27, the recommendation information according to the emotion state of the subject is also displayed on the screen of the terminal device 300. In the example of FIG. 27, the emotion state of the subject is “anger”. For example, a face letter or an icon indicating the emotion state of the subject may be displayed on the screen of the terminal device 300. The subject who has visually recognized the emotion state displayed on the screen can confirm his/her emotion state. The subject who has visually recognized the recommendation information displayed on the screen can bring his/her emotion state close to a normal state by paying attention to the recommendation information. However, the recommendation information displayed on the screen does not necessarily cause the subject to change the emotion state as expected. For example, the estimated emotion state of the subject may be transmitted to a terminal device (not illustrated) owned by a family member or an acquaintance of the subject. With this configuration, there is a possibility that the emotion state of the subject can be brought closer to the normal state according to the behavior of another person in a close relationship with the subject instead of the inorganic information displayed on the screen.

In the example of FIG. 27, a flower image is also displayed on the screen of the terminal device 300 in order to soften the emotion state of the subject toward a normal state. The image to be displayed on the screen may be any image as long as there is a possibility of softening the emotion state of the subject. What is displayed on the screen of the terminal device 300 may be not only an image but also a video. Music that softens the emotion state of the subject may be played from a speaker (not illustrated) of the terminal device 300. For example, in a case where the emotion state of the subject is “sorrow”, content such as an image, a video, and music that comfort the subject may be provided to the subject. For example, in a case where the emotion state of the subject is “pleasure” or “delight”, content that maintains the emotion state may be provided to the subject. The content provided to the subject is preferably set for each emotion of the subject. For example, a function of inputting whether the provided information is adapted to the subject’s emotion may be added. When it is configured to train the user’s reaction to information provided according to the estimated emotion and feed back to the emotion estimation thereafter, the emotion of the subject can be estimated more accurately.

For example, the optical sensor 30 may be attached to a driver of an automobile, and recommendation information according to an emotion state of the driver may be provided. For example, a safe driving environment can be provided by recommending the driver to take a break or notifying the driver of a predicted arrival time to the next parking area according to the estimation result of the emotion state of the driver. For example, in a case where the emotion state of the driver of the automobile is “anger” or “sorrow”, music or a message for soothing or comforting the driver’s emotion may be played. For example, in a case where the emotion state of the driver of the automobile is “delight”, music or a message prompting the driver to have some tension may be played. For example, in a case where the emotion state of the driver of the automobile is “pleasure”, music or a message that is likely to maintain the emotion state may be played. For example, recommendation information according to a driver’s emotion state and driving time may be provided. For example, in a case where driving time is long and a tendency of “anger” appears in emotion, recommendation information such as “go to next parking region and rise up and exercise” may be provided to the driver. For example, in a case where driving time is long and a tendency of “sorrow” appears in emotions, recommendation information such as “go to next parking region and sleep” may be provided to the driver.

For example, the attention distraction level of the driver may be estimated based on the emotion state of the driver. The attention distraction level tends to be high in an extreme emotion state. Therefore, for example, in a case where the awakeness level or the emotional valence is extremely large or extremely small, the attention distraction level is estimated to be high. A threshold value related to the attention distraction level may be set for the awakeness level or the emotional valence, and the attention distraction level of the driver may be estimated according to the relationship with the threshold value. For example, in a case where the attention distraction level exceeds a threshold value, a notification sound for calling attention may be emitted.

For example, the optical sensor 30 may be worn by a user who lives a daily life, and recommendation information according to the emotion state of the subject may be provided. For example, in a case where the emotion state of the user is “anger” or “sorrow”, recommendation information recommending exercise such as walking or running may be provided in order to distract the user. For example, in a case where the user’s emotion state is “anger” or “sorrow”, music or information that makes it easy to shift the user’s emotion state to “delight” or “pleasure” may be provided. For example, in a case where the user’s emotion state is “delight” or “pleasure”, music or information that can increase the emotion state may be provided. For example, in a case where the emotion state of the user is “delight” or “pleasure”, obstructive information may not be provided in such a way that the environment at that time is maintained.

As described above, the biological information estimation system of the present example embodiment includes the optical sensor, the measurement device, and the estimation device. The optical sensor is the optical sensor of the first or second example embodiment. The measurement device is the measurement device of the first or second example embodiment. The estimation device acquires biological data of the subject measured by the measurement device. The estimation device estimates biological information about the subject based on the acquired biological data. According to the present example embodiment, the biological information of the subject can be estimated using the biological data measured by the measurement device.

In an aspect of the present example embodiment, the measurement device measures the pulse signal of the subject as the biological data. The estimation device estimates the pulse rate of the subject using the pulse signal of the subject. The estimation device outputs information related to the estimated pulse rate. According to the present aspect, for example, by displaying the pulse rate estimated using the biological data measured by the measurement device on the screen, a person viewing the screen can confirm the pulse rate of the subject.

In an aspect of the present example embodiment, the estimation device estimates the emotion state of the subject using the pulse signal of the subject. The estimation device outputs information related to the estimated emotion state. According to the present aspect, for example, by displaying the emotion state estimated using the biological data measured by the measurement device on the screen, a person viewing the screen can confirm the emotion state of the subject.

Fourth Example Embodiment

Figure 28:
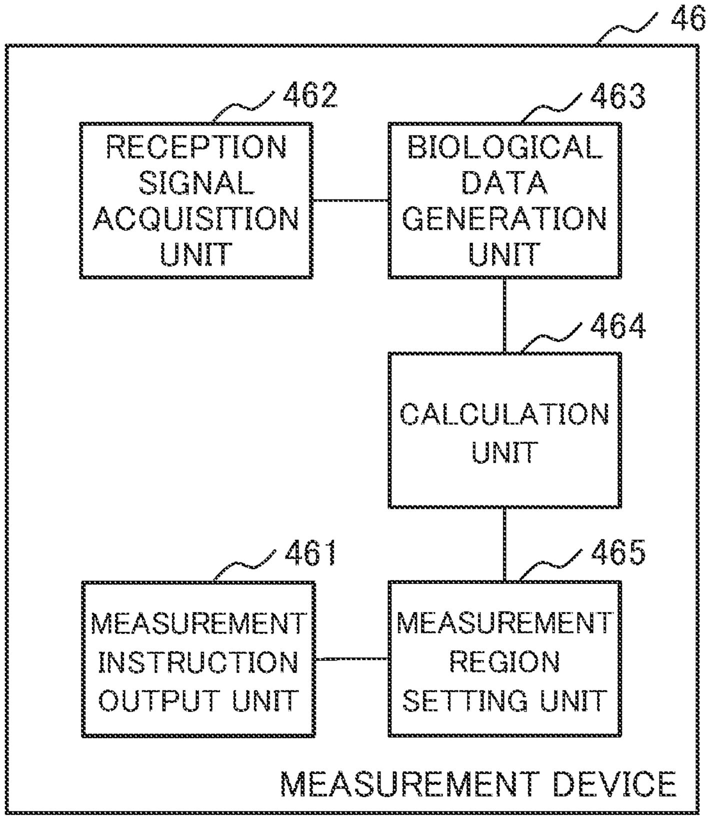
FIG. 28 is a block diagram illustrating an example of a configuration of a measurement device according to a fourth example embodiment.

Next, the measurement device according to a fourth example embodiment will be described with reference to the drawings. The measurement device of the present example embodiment has a configuration in which the first to third measurement devices and the measurement unit are simplified. FIG. 28 is a block diagram illustrating an example of a configuration of a measurement device 46 according to the present example embodiment. The measurement device 46 includes a measurement instruction output unit 461, a reception signal acquisition unit 462, a biological data generation unit 463, a calculation unit 464, and a measurement region setting unit 465.

The measurement instruction output unit 461 outputs a measurement instruction including a first measurement instruction to instruct first measurement corresponding to preliminary measurement and a second measurement instruction to instruct second measurement corresponding to main measurement to an optical sensor including a light receiving element array in which a plurality of light receiving elements is two-dimensionally disposed. The reception signal acquisition unit 462 acquires a reception signal of at least one of the plurality of light receiving elements according to the measurement instruction. The biological data generation unit 463 generates biological data for each light receiving element using the acquired reception signal. The calculation unit 464 calculates the deviation of the biological data for each light receiving element using the reception signal acquired in response to the first measurement instruction. The measurement region setting unit 465 sets the measurement region including the light receiving element used for the second measurement according to the second measurement instruction according to the deviation of the biological data for each light receiving element.

In the present example embodiment, in the measurement of the biological data using the optical sensor, the measurement region including the light receiving element used for the second measurement corresponding to the main measurement is set according to the deviation of the biological data for each light receiving element. According to the present example embodiment, in the second measurement corresponding to the main measurement, it is possible to reduce the load of measurement and communication by the optical sensor. Therefore, according to the present example embodiment, it is possible to constantly measure biological data using the optical sensor.

(Hardware) A hardware configuration for executing control and processing according to each example embodiment of the present disclosure will be described using an information processing device 90 of FIG. 29 as an example. The information processing device 90 in FIG. 29 is a configuration example for performing control and a process of each example embodiment, and does not limit the scope of the present disclosure.

Figure 29:
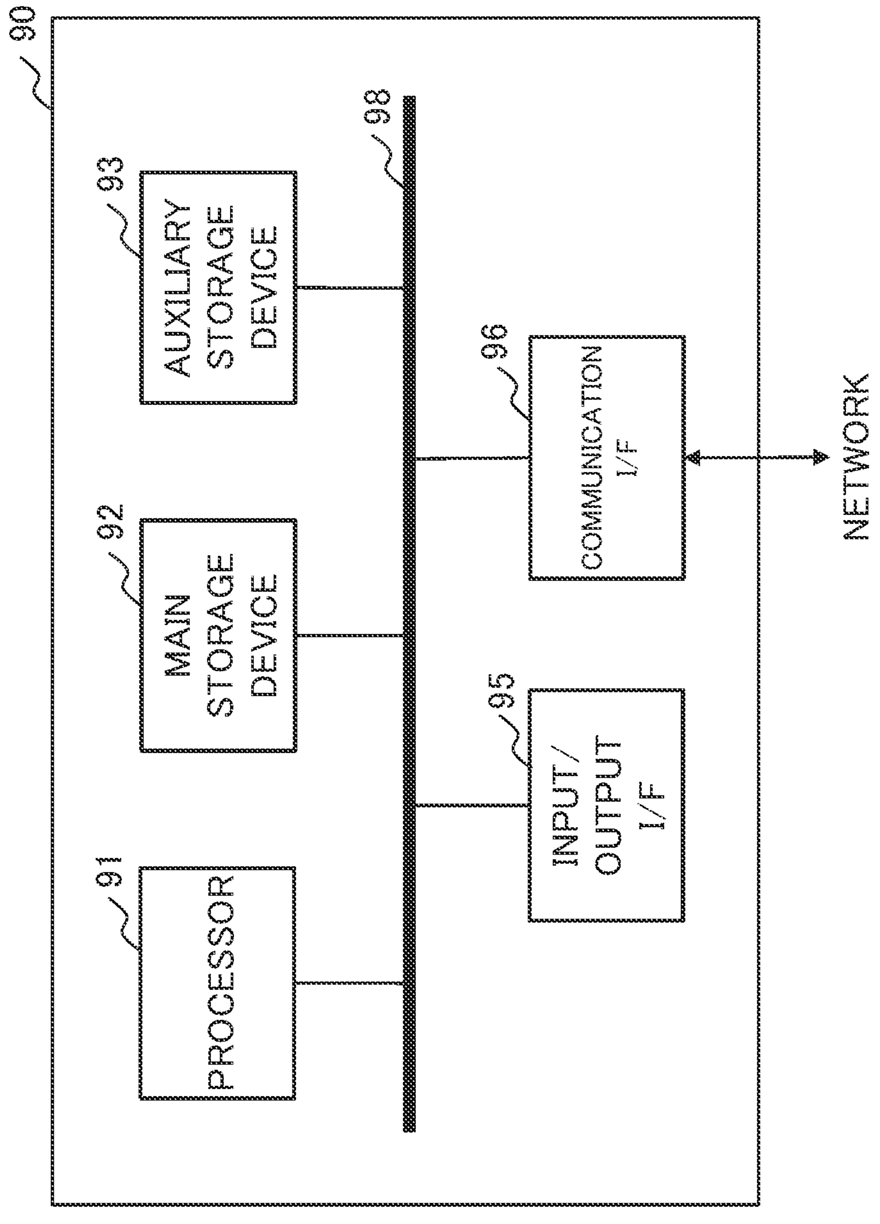
FIG. 29 is a block diagram illustrating an example of a hardware configuration that implements control and processing of each example embodiment.

As illustrated in FIG. 29, the information processing device 90 includes a processor 91, a main storage device 92, an auxiliary storage device 93, an input/output interface 95, and a communication interface 96. In FIG. 29 the interface is abbreviated as an interface (I/F). The processor 91, the main storage device 92, the auxiliary storage device 93, the input/output interface 95, and the communication interface 96 are data-communicably connected to each other via a bus 98. The processor 91, the main storage device 92, the auxiliary storage device 93, and the input/output interface 95 are connected to a network such as the Internet or an intranet via the communication interface 96.

The processor 91 develops the program stored in the auxiliary storage device 93 or the like in the main storage device 92. The processor 91 executes the program developed in the main storage device 92. In the present example embodiment, a software program installed in the information processing device 90 may be used. The processor 91 executes control and processing according to each example embodiment.

The main storage device 92 has a region in which a program is developed. A program stored in the auxiliary storage device 93 or the like is developed in the main storage device 92 by the processor 91. The main storage device 92 is achieved by, for example, a volatile memory such as a dynamic random access memory (DRAM). A nonvolatile memory such as a magnetoresistive random access memory (MRAM) may be configured and added as the main storage device 92.

The auxiliary storage device 93 stores various pieces of data such as programs. The auxiliary storage device 93 is achieved by a local disk such as a hard disk or a flash memory. Various pieces of data may be stored in the main storage device 92, and the auxiliary storage device 93 may be omitted.

The input/output interface 95 is an interface that connects the information processing device 90 with a peripheral device based on a standard or a specification. The communication interface 96 is an interface that connects to an external system or a device through a network such as the Internet or an intranet in accordance with a standard or a specification. The input/output interface 95 and the communication interface 96 may be shared as an interface connected to an external device.

An input device such as a keyboard, a mouse, or a touch panel may be connected to the information processing device 90 as necessary. These input devices are used to input of information and settings. In a case where the touch panel is used as the input device, the display screen of the display device may also serve as the interface of the input device. Data communication between the processor 91 and the input device may be mediated by the input/output interface 95.

The information processing device 90 may be provided with a display device that displays information. In a case where a display device is provided, the information processing device 90 preferably includes a display control device (not illustrated) that controls display of the display device. The display device may be connected to the information processing device 90 via the input/output interface 95.

The information processing device 90 may be provided with a drive device. The drive device mediates reading of data and a program from the storage medium, writing of a processing result of the information processing device 90 to the storage medium, and the like between the processor 91 and the storage medium (program storage medium). The drive device may be connected to the information processing device 90 via the input/output interface 95.

The above is an example of a hardware configuration for enabling control and processing according to each example embodiment of the present invention. The hardware configuration of FIG. 29 is an example of a hardware configuration for executing control and processing according to each example embodiment, and does not limit the scope of the present invention. A program for causing a computer to execute control and processing according to each example embodiment is also included in the scope of the present invention. A program storage medium in which the program according to each example embodiment is recorded is also included in the scope of the present invention. The storage medium can be achieved by, for example, an optical storage medium such as a compact disc (CD) or a digital versatile disc (DVD). The storage medium may be achieved by a semiconductor storage medium such as a Universal Serial Bus (USB) memory or a secure digital (SD) card. The storage medium may be achieved by a magnetic storage medium such as a flexible disk, or another storage medium. In a case where the program executed by the processor is recorded in the storage medium, the storage medium corresponds to a program storage medium.

The components of each example embodiment may be combined in any manner. The components of each example embodiment may be achieved by software or may be achieved by a circuit.

While the present invention is described with reference to example embodiments thereof, the present invention is not limited to these example embodiments. Various modifications that can be understood by those of ordinary skill in the art can be made to the configuration and details of the present invention within the scope of the present invention.

Some or all of the above example embodiments may be described as the following Supplementary Notes, but are not limited to the following.

Supplementary Note 1

A measurement device including a measurement instruction output unit that outputs, to an optical sensor including a light receiving element array in which a plurality of light receiving elements is two-dimensionally arranged, a measurement instruction including a first measurement instruction to instruct first measurement corresponding to preliminary measurement and a second measurement instruction to instruct second measurement corresponding to main measurement, a reception signal acquisition unit that acquires a reception signal of at least one of the plurality of light receiving elements according to the measurement instruction, a biological data generation unit that generates biological data for each of the light receiving elements using the acquired reception signal, a calculation unit that calculates a deviation of the biological data for each of the light receiving elements using the reception signal acquired according to the first measurement instruction, and a measurement region setting unit that sets a measurement region including a light receiving element used for second measurement according to the second measurement instruction in accordance with the deviation of the biological data for each of the light receiving elements.

Supplementary Note 2

The measurement device according to Supplementary Note 1, wherein the measurement instruction output unit outputs, to the optical sensor, the first measurement instruction to instruct measurement using all of the plurality of light receiving elements constituting the light receiving element array and the second measurement instruction to instruct measurement using a light receiving element within a range of the measurement region among the plurality of light receiving elements constituting the light receiving element array.

Supplementary Note 3

The measurement device according to Supplementary Note 1 or 2, wherein the calculation unit calculates a difference between a representative value of the biological data for each of the light receiving elements and a representative value of all the biological data of the plurality of light receiving elements as the deviation of the biological data for each of the light receiving elements, and wherein the measurement region setting unit sets a measurement candidate region according to the deviation of the biological data for each of the light receiving elements, and sets the measurement region within a range of the measurement candidate region.

Supplementary Note 4

The measurement device according to Supplementary Note 3, wherein the measurement region setting unit sets a region including a light receiving element in which the deviation of the biological data for each light receiving element exceeds a predetermined threshold value as the measurement candidate region.

Supplementary Note 5

The measurement device according to Supplementary Note 4, wherein the calculation unit calculates a standard deviation of the deviations of the biological data regarding all of the plurality of light receiving elements, and wherein the measurement region setting unit sets, as the measurement candidate region, a region including a light receiving element in which the deviation is equal to or more than predetermined times the standard deviation, and sets the measurement region within a range of the measurement candidate region.

Supplementary Note 6

The measurement device according to any one of Supplementary Notes 3 to 5, wherein the calculation unit calculates a difference between a representative value of the biological data for each of a plurality of calculation regions including the plurality of light receiving elements and an average value of representative values of the biological data for all of the plurality of calculation regions as a region deviation of the biological data for each of the calculation regions, and wherein the measurement region setting unit sets the measurement candidate region according to the region deviation of the biological data for each calculation region.

Supplementary Note 7

The measurement device according to any one of Supplementary Notes 1 to 6, wherein the measurement instruction output unit outputs, to the optical sensor, the first measurement instruction to update the measurement region at a timing when a predetermined period has elapsed since the main measurement according to the second measurement instruction was started.

Supplementary Note 8

The measurement device according to any one of Supplementary Notes 1 to 7, wherein the measurement instruction output unit outputs the first measurement instruction to the optical sensor to update the measurement region when a measurement value of the biological data falls below a reference value in the main measurement according to the second measurement instruction.

Supplementary Note 9

The measurement device according to Supplementary Note 7 or 8, wherein when the measurement region is updated, the measurement instruction output unit outputs the first measurement instruction including an instruction to perform the preliminary measurement by narrowing a region to a peripheral region of the measurement region and the measurement region to the optical sensor.

Supplementary Note 10

The measurement device according to any one of Supplementary Notes 1 to 9, wherein when the measurement value of the biological data is interrupted in the main measurement according to the second measurement instruction, the measurement region setting unit resets a region having a high rank of the deviation as the measurement region, and wherein the measurement instruction output unit outputs, to the optical sensor, the second measurement instruction including an instruction to continue measurement in the reset measurement region.

Supplementary Note 11

The measurement device according to any one of Supplementary Notes 1 to 10, further including a biological data output unit that outputs the biological data measured in the main measurement according to the second measurement instruction.

Supplementary Note 12

The measurement device according to Supplementary Note 11, wherein the biological data output unit outputs a heat map in which the measurement region is highlighted in association with a light receiving face of the light receiving element array.

Supplementary Note 13

An optical sensor including the measurement device according to any one of Supplementary Notes 1 to 12, a plurality of light emitters that is disposed on a measurement face of a substrate attached to a skin of a subject whose biological data is to be measured and each of which emits an optical signal toward the skin of the subject, a light receiving element array that is disposed on the measurement face of the substrate and in which a plurality of light receiving elements that receives reflected light of the optical signal emitted from each of the plurality of light emitters is two-dimensionally disposed, and a control unit that causes each of the plurality of light emitters to emit the optical signal according to a measurement instruction from the measurement device, receive a reception signal for each of the light receiving elements according to reflected light of the optical signal received by each of the plurality of light receiving elements constituting the light receiving element array, output the received reception signal for each of the light receiving elements to the measurement device, and output the reception signal by a light receiving element within a range of a measurement region set by the measurement device to the measurement device in a main measurement period according to a second measurement instruction from the measurement device.

Supplementary Note 14

A biological data measurement system including the measurement device according to any one of Supplementary Notes 1 to 12, and an optical sensor including a plurality of light emitters that is disposed on a measurement face of a substrate attached to a skin of a subject whose biological data is to be measured and each of which emits an optical signal toward the skin of the subject, a light receiving element array that is disposed on the measurement face of the substrate and in which a plurality of light receiving elements that receives reflected light of the optical signal emitted from each of the plurality of light emitters is two-dimensionally disposed, and a control unit that causes each of the plurality of light emitters to emit the optical signal according to a measurement instruction from the measurement device, receive a reception signal for each of the light receiving elements according to reflected light of the optical signal received by each of the plurality of light receiving elements constituting the light receiving element array, output the received reception signal for each of the light receiving elements to the measurement device, and output the reception signal by a light receiving element within a range of a measurement region set by the measurement device to the measurement device in a main measurement period according to a second measurement instruction from the measurement device.

Supplementary Note 15

A biological information estimation system including the measurement device according to any one of Supplementary Notes 1 to 12, and an estimation device that acquires biological data of a subject measured by the measurement device, and estimates biological information of the subject based on the acquired biological data.

Supplementary Note 16

The biological information estimation system according to Supplementary Note 15, wherein the measurement device measures a pulse signal of the subject as the biological data, and wherein the estimation device estimates a pulse rate of the subject using the pulse signal of the subject and outputs information corresponding to the estimated pulse rate.

Supplementary Note 17

The biological information estimation system according to Supplementary Note 16, wherein the estimation device estimates an emotion state of the subject using the pulse signal of the subject and outputs information corresponding to the estimated emotion state.

Supplementary Note 18

A measurement method executed by a computer, the method including outputting, to an optical sensor including a light receiving element array in which a plurality of light receiving elements is two-dimensionally arranged, a measurement instruction including a first measurement instruction to instruct first measurement corresponding to preliminary measurement and a second measurement instruction to instruct second measurement corresponding to main measurement, acquiring a reception signal of at least one of the plurality of light receiving elements according to the measurement instruction, generating biological data for each of the light receiving elements using the acquired reception signal, calculating a deviation of the biological data for each of the light receiving elements using the reception signal acquired according to the first measurement instruction, and setting a measurement region including a light receiving element used for second measurement according to the second measurement instruction in accordance with the deviation of the biological data for each of the light receiving elements.

Supplementary Note 19

A program for causing a computer to execute the steps of outputting, to an optical sensor including a light receiving element array in which a plurality of light receiving elements is two-dimensionally arranged, a measurement instruction including a first measurement instruction to instruct first measurement corresponding to preliminary measurement and a second measurement instruction to instruct second measurement corresponding to main measurement, acquiring a reception signal of at least one of the plurality of light receiving elements according to the measurement instruction, generating biological data for each of the light receiving elements using the acquired reception signal, calculating a deviation of the biological data for each of the light receiving elements using the reception signal acquired according to the first measurement instruction, and setting a measurement region including a light receiving element used for second measurement according to the second measurement instruction in accordance with the deviation of the biological data for each of the light receiving elements.

REFERENCE SIGNS LIST

1 biological data measurement system
3 biological information estimation system
10, 20, 30 optical sensor
11, 21 light emitter
12, 22 light receiving element array
13, 23 control unit
16, 36, 46 measurement device
37 estimation device
100, 300 terminal device
110 substrate
111 adhesive layer
131, 231 measurement instruction acquisition unit

132, 232 light emission control unit
133, 233 storage unit
134, 234 signal acquisition unit
135, 235 signal output unit
161, 461 measurement instruction output unit
162, 462 reception signal acquisition unit
163, 463 biological data generation unit
164, 464 calculation unit
165, 465 measurement region setting unit
166 biological data output unit
236 measurement unit
340 training device
370 estimation model

What is claimed is:

1. A measurement device comprising:

a memory storing instructions; and a processor connected to the memory and configured to execute the instructions to:

output, to an optical sensor including a light receiving element array in which a plurality of light receiving elements is two-dimensionally arranged, a measurement instruction including a first measurement instruction to instruct first measurement corresponding to preliminary measurement and a second measurement instruction to instruct second measurement corresponding to main measurement;

acquire a reception signal of at least one of the plurality of light receiving elements according to the measurement instruction;

generate biological data for each of the light receiving elements using the acquired reception signal;

calculate a deviation of the biological data for each of the light receiving elements using the biological data generated using the reception signal acquired according to the first measurement instruction; and set a measurement region including a light receiving element used for second measurement according to the second measurement instruction in accordance with the deviation of the biological data for each of the light receiving elements, wherein the processor is configured to execute the instructions to calculate a difference between a representative value of the biological data for each of the light receiving elements and a representative value of all the biological data of the plurality of light receiving elements as the deviation of the biological data for each of the light receiving elements, set a measurement candidate region according to the deviation of the biological data for each of the light receiving elements, and set the measurement region within a range of the measurement candidate region.

2. The measurement device according to claim 1, wherein the processor is configured to execute the instructions to output, to the optical sensor, the first measurement instruction to instruct measurement using all of the plurality of light receiving elements constituting the light receiving element array and the second measurement instruction to instruct measurement using a light receiving element within a range of the measurement region among the plurality of light receiving elements constituting the light receiving element array.

3. The measurement device according to claim 1, wherein the processor is configured to execute the instructions to set a region including a light receiving element in which the deviation of the biological data for each light receiving element exceeds a predetermined threshold value as the measurement candidate region.

4. The measurement device according to claim 3, wherein the processor is configured to execute the instructions to calculate a standard deviation of the deviations of the biological data regarding all of the plurality of light receiving elements, set, as the measurement candidate region, a region including a light receiving element in which the deviation is equal to or more than predetermined times the standard deviation, and set the measurement region within a range of the measurement candidate region.

5. The measurement device according to claim 1, wherein the processor is configured to execute the instructions to calculate a difference between a representative value of the biological data for each of a plurality of calculation regions including the plurality of light receiving elements and an average value of representative values of the biological data for all of the plurality of calculation regions as a region deviation of the biological data for each of the calculation regions, and set the measurement candidate region according to the region deviation of the biological data for each calculation region.

6. The measurement device according to claim 1, wherein the processor is configured to execute the instructions to output, to the optical sensor, the first measurement instruction to update the measurement region at a timing when a predetermined period has elapsed since the second measurement according to the second measurement instruction was started.

7. The measurement device according to claim 6, wherein when the measurement region is updated, the processor is configured to execute the instructions to output the first measurement instruction including an instruction to perform the first measurement by narrowing a region to a peripheral region of the measurement region and the measurement region to the optical sensor.

8. The measurement device according to claim 1, wherein the processor is configured to execute the instructions to output the first measurement instruction to the optical sensor to update the measurement region when a measurement value of the biological data falls below a reference value in the second measurement according to the second measurement instruction.

9. The measurement device according to claim 1, wherein when the measurement value of the biological data is interrupted in the second measurement according to the second measurement instruction, the processor is configured to execute the instructions to reset a region having a high rank of the deviation as the measurement region, and output, to the optical sensor, the second measurement instruction including an instruction to continue measurement in the reset measurement region.

10. The measurement device according to claim 1, wherein the processor is configured to execute the instructions to output the biological data measured in the second measurement according to the second measurement instruction.

11. The measurement device according to claim 10, wherein the processor is configured to execute the instructions to output a heat map in which the measurement region is highlighted in association with a light receiving face of the light receiving element array.

12. A biological data measurement system comprising:

the measurement device according to claim 1; and an optical sensor including a plurality of light emitters that is disposed on a measurement face of a substrate adapted to be attached to a skin of a subject whose biological data is to be measured and each of which emits an optical signal toward the skin of the subject, a light receiving element array that is disposed on the measurement face of the substrate and in which a plurality of light receiving elements that receives reflected light of the optical signal emitted from each of the plurality of light emitters is two-dimensionally disposed, and a controller comprising a memory storing instructions; and a processor connected to the memory of the controller and configured to execute the instructions to cause each of the plurality of light emitters to emit the optical signal according to a measurement instruction from the measurement device, receive a reception signal for each of the light receiving elements according to reflected light of the optical signal received by each of the plurality of light receiving elements constituting the light receiving element array, output the received reception signal for each of the light receiving elements to the measurement device, and output the reception signal by a light receiving element within a range of a measurement region set by the measurement device to the measurement device in a second measurement period according to a second measurement instruction from the measurement device.

13. A biological information estimation system comprising:

the measurement device according to claim 1; and an estimation device comprising a memory storing instructions; and a processor connected to the memory of the estimation device and configured to execute the instructions to acquire biological data of a subject measured by the measurement device, and estimate biological information of the subject based on the acquired biological data.

14. The biological information estimation system according to claim 13, wherein the processor of the measurement device is configured to execute the instructions to measure a pulse signal of the subject as the biological data, and wherein the processor of the estimation device is configured to execute the instructions to estimate a pulse rate of the subject using the pulse signal of the subject, and output information corresponding to the estimated pulse rate.

15. The biological information estimation system according to claim 14, wherein the processor of the estimation device is configured to execute the instructions to estimate an emotion state of the subject using the pulse signal of the subject, and output information corresponding to the estimated emotion state.

16. The biological information estimation system according to claim 14, wherein the processor of the estimation device is configured to execute the instructions to estimate an emotion state of the subject using the pulse signal of the subject by using an estimation model learned by machine learning, and display information that supports the subject for making decision about taking an action corresponding to the estimated emotion state.

17. A measurement method executed by a computer, the method comprising:

outputting, to an optical sensor including a light receiving element array in which a plurality of light receiving elements is two-dimensionally arranged, a measurement instruction including a first measurement instruction to instruct first measurement corresponding to preliminary measurement and a second measurement instruction to instruct second measurement corresponding to main measurement;

acquiring a reception signal of at least one of the plurality of light receiving elements according to the measurement instruction;

generating biological data for each of the light receiving elements using the acquired reception signal;

calculating a deviation of the biological data for each of the light receiving elements using the biological data generated using the reception signal acquired according to the first measurement instruction; and setting a measurement region including a light receiving element used for second measurement according to the second measurement instruction in accordance with the deviation of the biological data for each of the light receiving elements, wherein the calculating the deviation includes calculating a difference between a representative value of the biological data for each of the light receiving elements and a representative value of all the biological data of the plurality of light receiving elements as the deviation of the biological data for each of the light receiving elements, and the setting the measurement region includes setting a measurement candidate region according to the deviation of the biological data for each of the light receiving elements, and setting the measurement region within a range of the measurement candidate region.

18. A non-transitory storage medium storing a program for causing a computer to execute the steps of:

outputting, to an optical sensor including a light receiving element array in which a plurality of light receiving elements is two-dimensionally arranged, a measurement instruction including a first measurement instruction to instruct first measurement corresponding to preliminary measurement and a second measurement instruction to instruct second measurement corresponding to main measurement;

acquiring a reception signal of at least one of the plurality of light receiving elements according to the measurement instruction;

generating biological data for each of the light receiving elements using the acquired reception signal;

calculating a deviation of the biological data for each of the light receiving elements using the biological data generated using the reception signal acquired according to the first measurement instruction; and setting a measurement region including the light receiving element used for second measurement according to the second measurement instruction in accordance with the deviation of the biological data for each of the light receiving elements, wherein the calculating the deviation includes calculating a difference between a representative value of the biological data for each of the light receiving elements and a representative value of all the biological data of the plurality of light receiving elements as the deviation of the biological data for each of the light receiving elements, and the setting the measurement region includes setting a measurement candidate region according to the deviation of the biological data for each of the light receiving elements, and setting the measurement region within a range of the measurement candidate region.

* * * * *